US006969373B2

(12) United States Patent
Schwartz et al.

(10) Patent No.: US 6,969,373 B2
(45) Date of Patent: Nov. 29, 2005

(54) SYRINGE SYSTEM

(75) Inventors: Robert S. Schwartz, Excelsior, MN (US); Robert A. Van Tassel, Excelsior, MN (US); David R. Holmes, Excelsior, MN (US)

(73) Assignee: Tricardia, LLC, Excelsior, MN (US)

( * ) Notice: Subject to any disclaimer, the term of this patent is extended or adjusted under 35 U.S.C. 154(b) by 269 days.

(21) Appl. No.: 09/967,681

(22) Filed: Sep. 28, 2001

(65) Prior Publication Data

US 2003/0009132 A1 Jan. 9, 2003

Related U.S. Application Data

(60) Provisional application No. 60/295,701, filed on Jun. 4, 2001, and provisional application No. 60/283,799, filed on Apr. 13, 2001.

(51) Int. Cl.[7] ......................... A61M 5/178; A61M 1/00; A61B 17/00

(52) U.S. Cl. ............. 604/170.03; 604/152; 604/164.01; 604/164.05; 606/1

(58) Field of Search ........................... 604/265.1, 264.1, 604/164.01, 170.03, 264, 152, 528, 167.01, 110, 198, 164.1–164.04, 164.06, 167.02–167.04, 523–533, 535

(56) References Cited

U.S. PATENT DOCUMENTS

| | | |
|---|---|---|
| 3,076,457 A | 2/1963 | Copen |
| 3,945,379 A | 3/1976 | Pritz et al. |
| 4,351,335 A | 9/1982 | Whitney et al. |
| 4,411,657 A | 10/1983 | Galindo |
| 4,838,877 A | 6/1989 | Massau |
| 5,116,313 A | 5/1992 | McGregor |
| 5,254,106 A | 10/1993 | Feaster |
| 5,380,307 A | 1/1995 | Chee et al. |
| 5,603,703 A | 2/1997 | Elsberry et al. |

(Continued)

FOREIGN PATENT DOCUMENTS

| | | |
|---|---|---|
| CH | 538 868 | 8/1973 |
| EP | 0271775 A2 | 6/1988 |
| EP | 0699449 A1 | 3/1996 |
| EP | 0727187 A1 | 8/1996 |
| WO | WO 96/31247 A1 | 10/1996 |
| WO | WO 97/18004 A1 | 5/1997 |
| WO | WO 99/19016 A1 | 4/1999 |

*Primary Examiner*—Nicholas D. Lucchesi
*Assistant Examiner*—Roz Maiorino
(74) *Attorney, Agent, or Firm*—Inskeep IP Group, Inc.

(57) ABSTRACT

A medical device is provided having a needle or a catheter, insertable into a living body, which defines a plurality of holes in fluid communication with a central lumen. The holes may be of various patterns located and angled to create a desired injectate cloud pattern when an injectate is forced through the central lumen and through the plurality of holes. One embodiment provides various designs including a moveable sheath or stylet used to selectively occlude one or more of the holes while in use, thereby providing an operating physician a way to manipulate the cloud pattern anytime during the introduction of the injectate. A reducer may be used in conjunction with these needles which provides an increased degree of control when injecting very small quantities of fluid.

9 Claims, 13 Drawing Sheets

U.S. PATENT DOCUMENTS

| | | | | | |
|---|---|---|---|---|---|
| 5,643,228 | A | | 7/1997 | Schucart et al. | |
| 5,662,619 | A | | 9/1997 | Zarate | |
| 5,735,831 | A | | 4/1998 | Johnson et al. | |
| 5,746,714 | A | | 5/1998 | Salo et al. | |
| 5,800,407 | A | | 9/1998 | Eldor | |
| 5,810,778 | A | | 9/1998 | Hjertman | |
| 5,817,074 | A | | 10/1998 | Racz | |
| 5,957,901 | A | | 9/1999 | Mottola et al. | |
| 5,989,209 | A | | 11/1999 | Barrett | |
| 6,010,495 | A | * | 1/2000 | Tilton, Jr. | 606/1 |
| 6,162,202 | A | | 12/2000 | Sicurelli et al. | |
| 6,179,816 | B1 | | 1/2001 | Mottola et al. | |
| 6,197,002 | B1 | * | 3/2001 | Peterson | 604/164.01 |
| 6,210,376 | B1 | | 4/2001 | Grayson | |
| 6,224,608 | B1 | | 5/2001 | Ciccolella et al. | |
| 6,241,710 | B1 | | 6/2001 | VanTassel et al. | |
| 6,488,662 | B2 | * | 12/2002 | Sirimanne | 604/164.01 |
| 2002/0123723 | A1 | * | 9/2002 | Sorenson et al. | 604/164.01 |

* cited by examiner

SYRINGE SYSTEM

CROSS REFERENCE TO RELATED APPLICATIONS

This application claims priority to previously filed U.S. Provisional Application entitled "Syringe System", Ser. No. 60/295,701, filed on Jun. 4, 2001 and U.S. Provisional Application entitled "Passive Hydraulic Volume Reduction Device", Ser. No. 60/283,799, filed on Apr. 13, 2001.

BACKGROUND OF THE INVENTION

The present invention pertains generally to instruments used to inject medicaments or other materials into a body wall, tissue, chamber, or vessel. More particularly, a syringe system is provided that is capable of injecting, manually or automatically, precisely measured quantities of liquids into a body A plurality of needle designs are included for creating advantageously shaped or diffused clouds, streams, or jets of medicament, contrast agents or other liquids.

The direct introduction of a drug, compound, contrast agent, biologically active peptide, gene, gene vector, protein, or cells for therapy, into the tissues or cells of a patient can have significant therapeutic value. Injection has long been a popular, relatively non-invasive means for the direct introduction of various medicaments and other fluids and is becoming more popular as a means for non-invasive delivery of pharmaceutical preparations of peptides because it minimizes tissue trauma. Injection is also a practical delivery strategy for angiogenesis.

Angiogenesis is defined as the growth of new blood vessels. It is an important natural process occurring in the body, both in health and in disease. It occurs in the healthy body for healing wounds and for restoring blood flow to tissues after injury or insult. It can be affected by angiogenic growth factors such as VEGF (vascular endothelial growth factor) and Fibroblast Growth Factor (acidic or basic). Endothelial and vascular smooth muscle cells, and myocardial cells have low mitotic activity in normal adult coronary arteries and heart muscle. However, during growth and development, and under conditions of ischemia, hypoxia, inflammation or other stresses, these cells may begin to migrate and divide, especially in the microcirculation. This eventually results in the development of new intramuscular blood vessels. Naturally occurring endothelial growth factors with angiogenic potency, like FGF and VEGF, can induce angiogenesis by stimulating endothelial cell growth, differentiation and migration.

The delivery strategy of angiogenesis is a major issue limiting its widespread use. A number of strategies have been attempted but none have proven as practical as the transendomyocardial injection. Other approaches have certain disadvantages that make them less desirable. Intracoronary infusions, injection of angiogenic factors into the blood stream in the coronary arteries, while minimally invasive, cause systemic exposure to growth factors, which can have undesirable effects elsewhere in the body. In addition, intracoronary infusions cause little uptake of factors by the myocardium. Intrapericardial injections, injection of factors into the sac surrounding the heart, have potential to be used as a reservoir for continual delivery, but many receiving the treatment have also received CABG and no longer possess an intact pericardium. Also the procedure to make the injection is very difficult due to the anatomy of the pericardium. The transepicardial injection, injection directly into myocardium from the outside, requires open-chest surgery although there is potentially a thoracoscopic method, which is less invasive. The problems of the above approaches for delivery leave transendomyocardial injection as the approach that most reliably delivers the factors without waste of factors, open-chest surgery, or systemic exposure.

However, there are several problems with the current procedure of intramyocardial injection using a standard needle with a single end hole. First, a significant amount of material often exits the needle and leaves the myocardium retrogradely via the needle puncture tract. This phenomenon is hereafter referred to as "backflow". This is a serious problem in that the angiogenesis-promoting factors are extremely expensive and if they are not introduced into the target area, they do not serve their desired function. Additionally, systemic exposure could produce problems such a hypotension, as the drug may interact with other areas of the body.

Another problem with the current procedure has to do with poor distribution of the factors. Convincing evidence has been observed that a traditional needle has a poor distribution of factors to the heart during injection. It is apparent, therefore, that there is a need for diffusionary needle having multiple holes which provides a greater and more controllable distribution of injectate in the area of injection.

Furthermore, the above identified problem pertaining to poor distribution of the factors may also be attributed to a vacuum effect created in the myocardial area when the needle is removed. This vacuum effect may draw injectate from the surrounding tissue back into the track formed by the needle. This effect may be lessened by providing a needle design whereby the outside surface of the needle prevents a seal from forming between the surface of the needle and the surrounding tissue. A diffusionary needle having multiple holes formed in the outer surface, a needle with a scored outer surface, or a combination of the two reduces this effect.

Not necessarily specific to angiogenesis, traditional injection methods and devices have failed to give the operating physician an acceptable degree of control over the size, shape and distribution of the injectate cloud. Conventional needle designs deliver the injectate to a single target site, thereby depositing an often higher than desired concentration of injectate, which must distribute itself naturally. In the case of certain peptides and pharmaceuticals, a high deposit concentration is potentially toxic if the concentration is sufficient to produce a biological response to the injected agent.

More specifically, traditional needles define an inner lumen leading from a reservoir, such as a syringe, to an opening in a distal, sharpened point. Once the tip of the needle has reached a target site, a physician or machine forces injectate through the opening. Control is achieved only by varying the rate at which the fluid is forced through the needle. In the case of a manually operated syringe, control is an imprecise matter of dexterity and muscle control. The resulting cloud of injectate at the injection site has a shape largely controlled by the density of the surrounding tissue and the flow rate of the stream leaving the needle. Moreover, as the partial pressure of injectate at the needle tip becomes high, there is a tendency for the injectate to follow the needle as it is withdrawn, thereby leaving the target site.

Accordingly, there continues to be a need in the art for new and better needles and injection systems, or devices suitable for injection of controlled amounts of therapeutic or diagnostic substances without substantial loss of injectate and without substantial damage to tissue, even during repeat injections.

There is a particular need for needles that are adapted for attachment to various types of catheters for such controlled delivery of therapeutic substances at remote locations within the body.

There is also a need for a method and a device which significantly yet controllably reduces the minimum quantity of injectate which a manual or automatic syringe may deliver.

Further, there is a need for an injection system that provides control over the stream or streams of injectate leaving the needle or a catheter. More specifically, there is a need for a needle or catheter which gives the operator the ability to manipulate the resulting cloud of injectate while the fluid is flowing from the needle, without having to move the needle longitudinally or transversely and risk causing injury to the target site.

Summarily, there is a need for an injection device that gives control over the concentration, pattern, and location of the deposition of an injectate.

BRIEF SUMMARY OF THE INVENTION

Generally, the present invention overcomes many of the problems in the art by providing a medical device capable of creating a cloud of injectate, in tissue, having a predetermined shape, size and concentration. The device includes a needle system having at least one elongate member with a plurality of holes constructed and arranged to create the desired cloud shape when injectate is forced therethrough. Preferably two elongate, telescopically related members act together to create a desired cloud shape. There is also a provision for an in-line hydraulic reducer assembly which allows an easily controlled, relatively large volume of liquid to be used to provide the injecting force necessary to deliver an extremely small injection into body tissue.

The reducer and needle of the present invention can be adapted for attachment to such instruments as a manual or automatic syringe, or adapted for attachment to a controlled pressure source.

In another embodiment according to the present invention, there are provided assemblage(s) useful for injecting a medicament into a remote location of subject in need thereof. The assemblage comprises a needle with a sharp distal point, with or without a flow-through lumen, and a catheter with a diffusing distal portion attached to the distal end of the needle. Preferably, the distal end of the catheter has a plurality of holes constructed and arranged for delivery of an injectate over a relatively large area. This catheter is optimally coupled with a substantially solid needle such that the injectate exits through the holes in the catheter. Alternatively the distal end of the catheter is constructed of a porous polymer. Uses for this catheter are numerous but a particularly important example is the intravenous delivery of a contrast agent, or for use in high magnetic fields such as produced by magnetic resonance imaging methods. The remainder of the catheter is non-porous to assure that the medicament will be delivered only to tissue in contact with the porous or hole-defining portion of the catheter.

The needle and/or assemblage are ideally suited for injecting, into tissue, medicaments containing nucleic acid encoding a therapeutic agent (or living cells containing such nucleic acid). For example, the needle (when attached to an appropriate catheter) or assemblage can be used to inject medicament(s) into the wall of a beating heart or other internal organ, without substantial loss of the medicament at the surface of the body wall and without substantial damage to tissue at the injection site caused by injectate.

One embodiment of the present invention particularly suited for injecting medicaments into fibrous tissue, such as the myocardium, provides a method of injecting fluid comprising developing an optimal pressure wave which acts to prepare the tissue for injectate reception prior to delivery of an operative dose. The pressure waveform includes an initial pressure spike which tenderizes and somewhat separates the tissue, thereby creating receiving "planes" in the tissue that provide areas of lower resistance to injectate reception. After the initial pressure wave, an operative dose of the injectate is delivered at a pressure which is less than the initial spike. Additional subsequent spikes may be included in the waveform if necessary to maintain these planes or open new, additional planes.

In other embodiments of the present invention, there are provided other methods for injecting a medicament into tissue of a subject. One injection method comprises inserting the distal portion of the needle into the tissue of the subject and causing a stream of injectate to form a cloud of a predetermined shape and size in the surrounding tissue. The cloud shape and size are determined not only by the arrangement and angles of the holes in the needle, but also the amount of force used to deliver the injectate. By varying the pressure, a physician can advantageously utilize the turbulent flow patterns created within the needle which necessarily vary with pressure. Thus, not only the size of the cloud is altered by delivering an injectate at various pressures, the cloud shape changes as well.

Controlling the flow of injectate through the needle also allows the physician to control the concentration of injectate at the target site. With a given size and distribution of exit holes, driving injectate into the needle at a predetermined pressure will force it out of the needle and into the tissue in a corresponding, predictable, distribution pattern. More specifically, each flow rate through a given needle with a predetermined hole pattern will cause the fluid to interact with the hole size and the tissue in a unique manner to provide a predetermined cloud pattern. The total volume of distribution of the injectate, divided by the absolute amount of injectate delivered, will fix the injectate concentration of injectate in the target tissue at distances from the needle. This is true for drugs, proteins, viral or other particles, or cell delivery (e.g. stem cells, myocardial cells, or any other living cells, etc). Thus, not only can the pattern of inject be controlled, the concentration of injectate is readily controlled. Injection through such a needle with holes has two dependent variables: pressure and flow rate. Pressure and flow rate at any point along the interior of the needle by the holes and exit of injectate from the needle. The total volume is an independent variable, and so governs absolute concentration.

Additional control and flexibility is obtained by manipulating the stream as it is being introduced into the tissue. As introduced above, the present invention provides a plurality of sheath designs either outside or inside the needle, including sheaths defining openings in their side walls which are useable to alter or occlude the cloud patterns during operation. It is envisioned that either the sheath, or the needle-like member telescopically received by the sheath, could be sharpened to provide the piercing ability necessary to introduce the device into a body. For example, a sharpened sheath having a plurality of holes constructed and arranged to create a desired cloud pattern is provided in one embodiment. A stylet is telescopically or slideably received by the sharpened sheath which is sized to occlude holes as it passes thereunder. The stylet defines its own inner lumen which allows the injectate to flow through the stylet and out the holes. Rotation of the sheath relative to the needle and its holes will effect this change.

It can be seen that variations on this stylet arrangement can produce varying effects. For instance, if the stylet has solid side walls and an opening on its distal end, leading to the lumen, then the stylet will allow the injectate to flow freely through the stylet and out the holes of the sheath when the stylet is in a position proximally displaced from the most proximal holes. In this position the resulting cloud will achieve its maximum length. As the stylet is moved in a distal direction, it begins to occlude the holes, beginning with those holes most proximal and eventually occluding all of the holes when the stylet achieves a distal position. The cloud, thus, may be shortened during operation from the cloud's proximal extent.

Another embodiment provides a stylet with an opening or window defined in its side wall. If this stylet further has a closed distal end wall, the resulting effect is quite different. In the proximal position, no injectate will be able to escape the stylet and no cloud will result. As the stylet is advanced in a distal direction, the window will begin to align with certain holes. A cloud will thus begin to form at a proximal end and advance distally. If the window is elongate, injectate will continue to flow from the more proximal holes as the stylet is advanced distally. Therefore, more injectate will have flowed from the proximal holes than from the distal holes during the course of stylet travel. The resulting cloud will have a tear drop shape or frustoconical shape. If the window is only defined on one side of the stylet, the cloud will have more of a wedge shape. If the window is not elongate, rather it is long enough to open a one or only a few holes at a time, the proximal holes will become reoccluded as the distal holes become unobstructed and a ribbon cloud will result. Additional flexibility is achieved by combining similar variations of a needle with a plurality of holes and a surrounding sheath defining a window.

Similarly, rotational relative movement between the sheath and the member can be used to provide even more cloud formations. For example, a sheath having an angled window, such that the window forms either a spiral around the sheath or a window of distally increasing or decreasing width, disposed over a needle with a linear arrangement of holes, will provide rotational control to an operating physician over the resulting cloud size and shape. As the sheath rotates over the holes, different holes will be uncovered and covered and the cloud will change shape, size and location. This embodiment may provide less tissue trauma than a linearly moving sheath.

It can thus be seen that there are a variety of combinations of hole patterns and window or opening shapes that can act in concert to produce a large number of cloud shapes, all of which are considered within the scope of this invention. Moreover, the needle itself, and its hole pattern, may be a functional device independent of the need for a sheath.

These various injection devices may be particularly useful in fighting coronary artery disease. Coronary artery disease (CAD) remains the leading killer in America of both men and women, responsible for nearly half a million deaths a year. It is estimated that every twenty-nine seconds an American will suffer from a coronary event and every minute someone will die from one. People suffering from coronary artery disease exhibit many levels of its development. In earlier stages, angioplasty can be performed to temporarily fix the problem. However in later stages, extremely invasive procedures such as coronary artery bypass graft (CABG) surgery must be performed to insure survival of the patient. Approximately 30% of patients in need of CABG will not be able to receive the treatment due to a lack of availability of the necessary veins to perform the graft. Angiogenesis, the formation of new vessels, has been demonstrated conclusively in a variety of animal models, as well as in patients with CAD. Mentioned above, as the field of therapeutic coronary angiogenesis has matured from basic investigations to clinical trials, the need for a minimally invasive and effective delivery strategy has come into focus.

The present invention provides a minimally invasive treatment involving angiogenesis-inducing factors introduced to an ischemic heart by way of the diffusionary, multi-holed, needle on a catheter. The development of the needle of the present invention is an important step in developing a delivery strategy that will distribute growth factors or gene vectors to the border regions between ischemic and nonischemic areas. These growth factors can induce the endothelial cells to reperfuse ischemic areas of the heart. Studies have shown that intramyocardial injections, direct injections into the heart, provide the most specific delivery to the myocardium. However, injections made with a traditional end hole needle have proved ill suited for the task of distributing and retaining the angiogenic factors within the myocardium. The needles of the present invention are designed to deliver the drug more successfully than a standard needle.

In still another embodiment, the present invention provides an in-line volumetric reducer useable to advance a predetermined volume of liquid to an open end of a fluid delivery lumen. The reducer comprises a first cylinder having a proximal end defining a proximal opening and a distal end defining a distal opening. A second cylinder is operably associated with the first cylinder and has a proximal end defining a proximal opening and a distal end defining a distal opening. The second cylinder has a smaller diameter than the first cylinder. Operably disposed within the first and second cylinders, are first and second pistons, respectively. The first and second pistons are operably connected such that when the first piston travels a predetermined linear distance within the first respective cylinder, the second piston moves the same distance within the second cylinder. Insofar as the second cylinder is smaller than the first cylinder, the quantity of fluid pushed therefrom, when the piston is moved, is substantially smaller than the quantity of fluid used to push the first piston over the predetermined distance.

If the flow through the reducer is reversed, it acts as a flow amplifier. Specifically, a small amount of fluid entering the second cylinder and moving the second piston will result in the first piston expelling a larger amount of fluid from the first cylinder. Of course, doing so will result in a significant pressure drop across the device and may require significant input pressure, depending on the disparity in size between the first and second pistons.

One embodiment of the reducer provides a rigid connection fixing the first piston to the second piston. The cylinders are also fixed relative to each other such that the pistons are slideable relative to the cylinders. For example, a base plate may be provided for mounting the cylinders in axial alignment with each other. A connecting rod integrally connecting the pistons follows an axis of symmetry from one cylinder to the other cylinder.

Another embodiment of the reducer provides an integral connection between the distal end of the first cylinder and the proximal end of the second cylinder. This connection may include a wall spanning the difference in diameters between the two cylinders. To prevent a hydraulic lock, a vent is provided, either in this wall or in the distal end of the first cylinder. A stop is provided to prevent the piston from moving past the vent. The integral connection allows the first piston to be used to pull the second piston in a proximal direction. This would be advantageous when using the reducer for either aspiration of very small amounts of fluid, or for using the reducer to draw medicament from a vial attachable to the second chamber of the reducer. Such a draw could also be taken from a vial in the more traditional sense by inserting the end of a standard hypodermic needle into the vial and pulling the second piston proximally a predetermined distance. Additionally a bleed air valve may be provided to permit air bubbles to escape from the catheter prior to injection.

Another embodiment provides a second cylinder which is removably attachable to the first cylinder. This is advantageous because it allows precisely measured medicaments and other injectates to be packaged within the second cylinder. The first piston of this embodiment may have a member, such as a rod, extending distally from the distal side of the piston, which is constructed and arranged to abut the second piston of the attachable second cylinder and push thereon during operation. Alternatively, the member could extend proximally from the proximate side of the second piston for abutment against the distal side of the first piston.

In yet another embodiment, a first cylinder is provided which may be integral or an attachable to an automatic injection machine or syringe. A plurality of second cylinders are selectably indexable to become operatively associated with the first cylinder, giving a physician a wide range of reduction or amplification ratios from which to choose. An indexing motor may be associated with a rotatable or linearly moveable magazine of second cylinders such that software loaded into the automatic syringe may determine the appropriate second cylinder for a given desired injection volume and flow rate. This embodiment vastly increases the operating range of the automatic syringe device.

In operation, the method of providing a predetermined output volume from a lumen of a catheter for a given input volume comprises providing such a flow reducer in line with a catheter between the input and the output of the catheter. If the second cylinder is not prepackaged with medicament, it is necessary to fill the second cylinder, distal of the second piston, and the catheter extending distally therefrom, with the medicament or injectate. A predetermined amount of input fluid is then injected into the input side of the catheter, thereby moving the first piston a predetermined distance and causing the second piston to move a distance substantially equal to the predetermined distance. Doing so results in causing an amount of injectate to exit the catheter output, such as the end of a diffusing or cloud creating needle, which is equal to the ratio of the second piston area to the first piston area.

One skilled in the art would realize that the shape of the cylinders and pistons is a design consideration only and the present invention could be practiced using a variety of alternatively shaped vessels and pistons.

One skilled in the art will also realize that the needles, sheaths, catheters and reducers of the present invention provide a great deal of control to the operating physician. This control is further improved by the use of automatic injection devices, such as that introduced above and described in more detail herein. Additionally, it is envisioned that hand-held automatic injection devices be provided by the present invention and used with the various needle, catheter, and reducer embodiments described herein and defined by the scope of the claims. These hand-held injectors control flow rate of injectate and may be electrically powered, or powered, for example, by compressed air or a carbon dioxide gas cylinder, using gas pressure to force a piston for fluid injection, or mechanically powered by mechanisms such as a spring. The gas is preferably pressurized in a chamber to a fixed pressure, which when released advances the driving piston a given distance within a given time, forcing injectate from the needle. Thus, a fixed pressure flow relation is created that is used to drive the injectate into the tissue. Alternatively, other methods of energizing the piston are possible, such as a wound-spring. Such a system would provide controls to set volume of injection and injection flow rate.

It is a particular object of the present invention to provide devices and methods useful for simultaneously injecting a medicament from multiple orifices along an injection course, rather than delivering a bolus injection, as is the case with traditional hypodermic needles.

The applications of this technology are numerous and not meant to be limited by the descriptions herein as will be readily appreciated by those skilled in the art. For example, the teachings herein could be used for injecting brain malignancy (primary or metastatic), or for cellular therapy where it is important to place living cells at specific points in the body. The embodiments herein could also be used to deliver high concentrations of chemotherapy to gain a higher therapeutic ratio than would otherwise be possible with systemic injection. Additionally, local anesthesia could be more effectively delivered to an area of a predetermined size using a quantity more representative of the size of the area to be numbed. This is in contrast to injecting a concentration high enough to eventually diffuse and numb the desired area. Similarly, steroids could more effectively be delivered into joints using the same principles. Insulin could be injected with this mechanism, as could low molecular weight heparin or other potent anticoagulants, high concentrations of which can cause tissue damage, fibrosis, or bleeding.

Additionally, it is envisioned that the needles of the present invention be fitted with tissue grabbing hooks such as those presently used when a needle is intended to remain in a patient for extended periods and it is desired that the tissue grow around the needle and anchor it in place. In other words, the teachings herein of multiple holes and placement thereof could be adapted to various present needle designs.

DETAILED DESCRIPTION OF THE INVENTION

Figure 1:
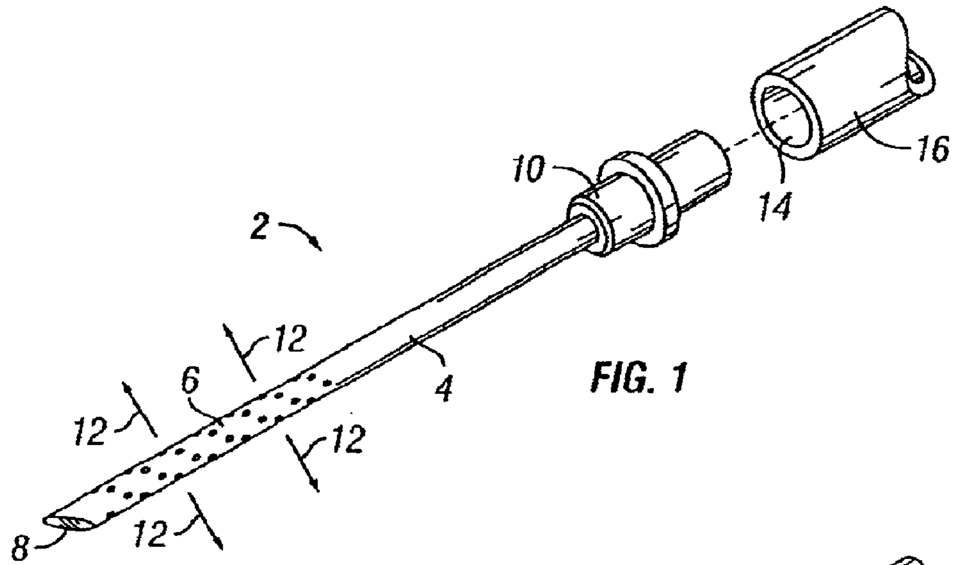
FIG. 1 is a schematic drawing showing an exploded view of the invention needle with weeping tip and a catheter to which it attaches.

The present invention overcomes many of the problems in the art by providing a needle and/or a catheter having a plurality of holes formed therethrough for micro or diffused injection of injectates, such as medicaments, living cells, contrast agents, or any liquid, into a body surface. The invention needle comprises a nonporous hollow needle shaft having a proximal end adapted to mate with an injection instrument, a porous or hole-based distal portion in fluid-tight connection to the needle shaft, and a point that is open, closed, or has a solid partial plug. The distal portion of the invention needle is adapted to cause a liquid injectate to weep, ooze, or form any desired 3-dimensional pattern therefrom multidirectionally under injection pressure with the distal portion and point of the needle are inserted into a tissue, chamber, or blood vessel. Typically, the length of the porous distal portion of the needle is determined by its intended use (e.g., whether intended for injecting medicament into a blood vessel or into a kidney, and the like). Alternatively, a solid needle is provided which is operatively attached to a catheter having a plurality of holes formed therethrough for introducing an injectate into a lumen in vivo over a relatively large area, thereby avoiding a point of high concentration. The needle or catheter could similarly be advantageously used for aspiration as the presence of a plurality of holes provides a low resistance fluid flow.

The invention needle with weeping tip can be adapted for attachment to such instruments as a syringe, or controlled pressure injector through a nonporous catheter. The assemblage of the needle and catheter is preferably steerable. For example, the needle can be attached to the distal tip of a steerable catheter (i.e., comprising a steering mechanism at the handle for controlling deflection of the distal tip section of the catheter shaft), some of which are known in the art for injection of medicaments into a remote body cavity or organ wall. Alternatively, the needle can be attached to a catheter with a porous distal portion and then the combination can be introduced into a steerable guidance catheter, such as is used in such techniques as angioplasty, angiogenic therapy such as angiogenic gene or protein injection, transmyocardial revascularization (TMR), percutaneous transmyocardial revascularization (PTMR), and the like, to direct the needle and catheter to the appropriate site for injection of a medicament. Guidance catheters suitable for use in the invention assemblages and methods are commercially available, for example from such vendors as Eclipse Technologies (Sunnyvale, Calif.) and CardioGenesis Corp. (Sunnyvale, Calif.).

In another embodiment according to the present invention, the distal portion of the needle is adapted with holes sized to create decreasing hydraulic impedance on injectate moving therethrough toward the point to cause a substantially uniform flow rate of injectate from the needle along with length thereof. The decrease in hydraulic impedance to injectate outflow can be of any type, for example, linear, exponential, Gaussian, and the like, and with a gradient in either longitudinal direction. The sharp point of the invention needle can be open, closed, or fitted with a solid partial plug to prevent the injectate from exiting as a single jet. If the point of the needle is open, the rate of flow from the open point can also be controlled by adjustment of the hydraulic impedance along the length of the distal portion of the needle to prevent the rate of fluid flow at the tip from substantially exceeding the rate of fluid flow along the porous portion adjacent to the point of the needle, as can be the hole size in the end of the needle Alternatively, the point of the needle can be open, but restricted by a solid partial plug so that the distal tip of the needle is designed to operate similarly to the tip of a garden nozzle wherein the solid partial plug cooperates with the open tip to restrict exit of fluid, thereby preventing exit of the fluid as a single jet.

The proximal end of the invention needle shaft is provided with a connector, such as a flange, hub, or the like, as is known in the art, for removable attachment of the needle to an instrument, such as a syringe or a catheter. The instrument serves as a reservoir or conduit for the fluid medicament. Therefore, the connector is such that there is fluid communication between the needle and the instrument. In use, the invention needle is mounted on the distal tip of the instrument, which is adapted to apply or transmit pressure to the medicament within the nonporous hollow shaft of the needle.

The holes may be formed in the needle using a cutting laser and techniques known in the art to punch holes into the needle segment (i.e. by a process of laser etching). The holes generally are, but need not be, circular. Also, the holes may taper in either direction from inside the needle to outside the needle. This will permit flow modification as the injectate exits the needle. The holes may be drilled in any direction to point fluid exit in directions making any arbitrary 3-dimensional pattern. The holes thus need not be perpendicular to the longitudinal axis of the needle.

In the embodiment of the invention illustrated in FIG. 1 herein, needle 2 has a nonporous hollow needle shaft, a porous distal portion 6 having inter-connecting pores and a closed sharp tip 8. Injectate 12 oozes from the pores in the distal portion under injection pressure. The sharp tip 8 of needle 2 is closed so that no injectate flows from the point of the needle. The proximal end of needle 2 is fitted with flange 10 for removable attachment to a catheter. The distal end of catheter 16, which has at least one open lumen 14 for passage of injectate into needle 2 attaches to the proximal end of needle 2. In other embodiments, a hub for mating with a syringe is substituted for the flange at the proximal end of the needle.

Figure 2:
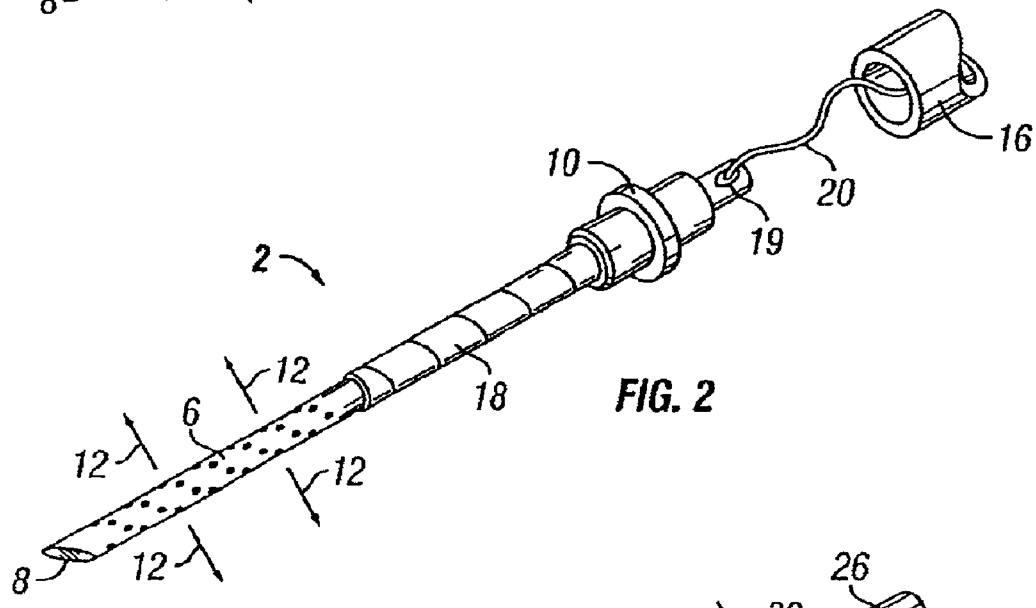
FIG. 2 is a schematic drawing showing the invention needle with the electrical connector for attachment to an electrocardiogram.

In another embodiment according to the present invention, the invention needle further comprises one or more sensor connectors for electrical attachment to an electrocardiogram. The electrocardiogram can be used to determine contact between the needle tip and the tissue, or if multiple electrodes are present, to determine the depth of penetration. In the embodiment shown in FIG. 2, the exterior of the needle shaft (not visible in this FIGURE) is coated with an insulator 18 and the connector 19 is attached directly to the proximal end (uncoated) of the needle shaft. Electrical lead 20 can be threaded down the lumen of a catheter for attachment to an electrocardiogram. Multiple leads can also be used in order to determine depth of the needle. In this configuration, the electrocardiogram is recorded from all leads. The larger signal is present from those ECG leads that are intramyocardial. Alternatively, the connector can be attached to the interior of the tip of the needle and catheter for attachment to an electrocardiogram. In this embodiment the needle itself acts as the electrode for the electrocardiogram and can be used for monopolar sensing of electrical currents or impedance within the heart, brain, nerves, proximal arteries, and the like. For monopolar sensing a return electrode can be provided by placing an ECG pad in electrical connection with the electrocardiogram on the exterior of the patient, for example on the exterior of the chest wall. It is also contemplated within the scope of the invention that a second electrode or sensor connector can be attached to the needle, for example to the exterior of the needle, spaced apart from the first electrode by at least about 0.5 mm, so as to provide two electrodes for sensing electrical currents within a subject's bodily organs. Multiple connectors can be used, and bipolar or multipolar electrical impedance sensed in this manner between/among the multiplicity of electrodes.

It is also possible that an electrode permanently implanted in a subject, such as belongs to a pacemaker, can be used as the return lead for remote bipolar sensing.

The advantages of using the invention needles to perform sensing are several. For example, for injection into a muscle or other organ that has electrical impulses running through it, an electrogram sensor attached to the invention needle can be used to confirm contact of the needle tip or proper insertion of the needle into the body wall of interest (e.g., the wall of a beating heart) before injection of the medicament into a treatment site. The depth of needle insertion into the tissue is determined by an array of electrodes. Those of skill in the art will realize that the invention needle having attached electrocardiogram sensor can also be used to judge whether such a prospective injection site is electrically active or not (i.e., whether the tissue is dead, hibernating due to lack of oxygen, or alive), and the like.

As with the needle described above, the size, and/or number, or density of holes in the catheter of the invention assemblage can be selected to create any desired gradient of injectate along the course of the injection path. For example, the size, and/or number or density of pores or holes can decrease along the length of the catheter moving towards the connection with the needle to allow for a substantially uniform rate of injectate flow along with length of the catheter. In this configuration, therefore, once the needle is used to thread the porous portion of the catheter through the tissue to be treated, a substantially uniform rate of fluid injection into surrounding tissues can be obtained along the injection course. Alternatively, or in conjunction with such a porosity gradient, the porous distal portion can also have a decreasing interior diameter along its length moving from the proximal end towards the connection with the needle to accomplish the same goal.

Figure 3:
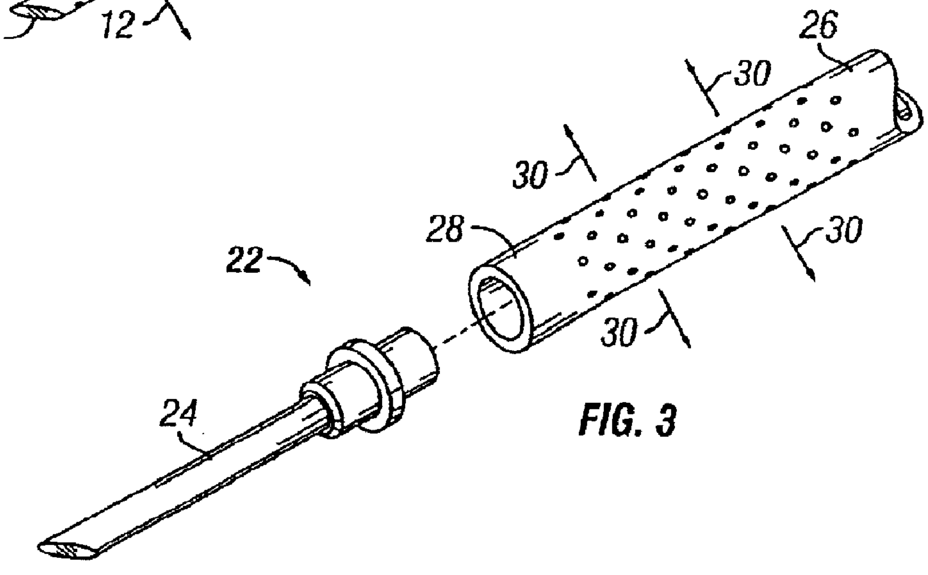
FIG. 3 is a schematic drawing showing the invention assemblage comprising a catheter and a needle, wherein the porous or hole pattern in the distal portion is located in the flexible catheter.

FIG. 3 herein illustrates the invention assemblage 22. Non-porous needle 24 with a closed tip is attached to the distal end of flexible catheter 26, which has a porous distal portion 28. Injectate 30 flows from the pores or holes in the flexible distal portion 28 of catheter 26.

As used herein, the terms "medicament(s)" and "injectate(s)" include all types of liquid substances (e.g., including solutions and suspensions) that have a beneficial therapeutic or diagnostic effects and use. Non-limiting examples of medicaments suitable for use in the invention methods include biologically active agents, such as small molecule drugs, proteinaceous substances, polynucleotides or nucleic acids (e.g. heterologous DNA, or RNA) and vectors (such as virus), liposomes, living cells including recombinant or bone marrow cells, and the like, containing such nucleic acids or polynucleotides, as well as liquid preparations or formulations thereof. Diagnostic injection of contrast or other diagnostic agents is also an additional application.

Figure 4:
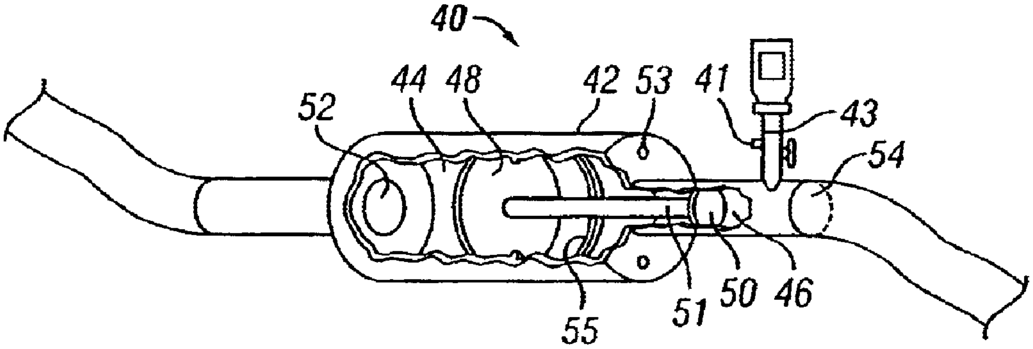
FIG. 4 is a perspective view of the reducer of the present invention.

FIG. 4 illustrates an embodiment of a preferred reduction device or reducer 40 of the present invention which is useful to control the amount of medicament or injectate that is delivered to the patient. Reducer 40 preferably includes a housing 42 which is constructed and arranged to form a proximal first chamber 44 and a distal second chamber 46 which has a smaller cross sectional area than that of the first chamber 44. A first piston 48 is slideably disposed within the first chamber 44 and a second piston 50 is slideably disposed within the second chamber 46.

The housing 42 defines a proximal opening 52 at the proximal end of the first chamber 44 which is attachable to a catheter. As used herein, the term "proximal" refers to the upstream side or operator/machine side whereas the term "distal" refers to the downstream or patient side of a component. The housing 42 also defines a distal opening 54 at the distal end of the second chamber 46 which is also attachable or integral to a catheter or needle. It is envisioned that the proximal and distal ends of the housing 42 could be attachable to catheters using threaded connections, luer locks, quick connections, friction fittings, or any suitable mechanism.

It can be seen that the first piston 48 is operably connected to the second piston 50 such that when the first piston 48 is moved a predetermined distance distally, the second piston 50 also moves. The embodiment in FIG. 4 uses a rod 51, which is integral with both the first piston 48 and the second piston 50. Because of the disparity in sizes of the respective pistons, and because the distances they move are the same, a hydraulic reducer is created. For any given input volume, the output volume is reduced by a ratio of the cross-sectional area of the second piston 50 divided by the cross-sectional area of the first piston 48. This is advantageous when it is desired to deliver a microinjection either manually, or using an automatic injection device such as that taught by U.S. Pat. No. 6,099,502, issued Aug. 8, 2000 to Duchon et al. Vents 53 are located in the distal end of the first chamber or cylinder 44 to allow air to escape as the first piston 48 is advanced distally. Without vents 53, a hydraulic lock would be created. A stop 55 is also provided to prevent the first piston 48 from traveling too far in a distal direction. Though shown in FIG. 4 as an annular ring, the stop 55 could be one or more inwardly extending protuberances, rods or similar formations extending distally from the first piston 48, or proximally from the end wall of the first cylinder 44, or even a similar arrangement associated with the second piston 50. It is important to prevent the first piston 48 from traveling distally past any vents 53 which may be formed in the side of the housing 42 because the pressurized fluid used to move the first piston 48 would leak through the vents 53.

Figure 5:
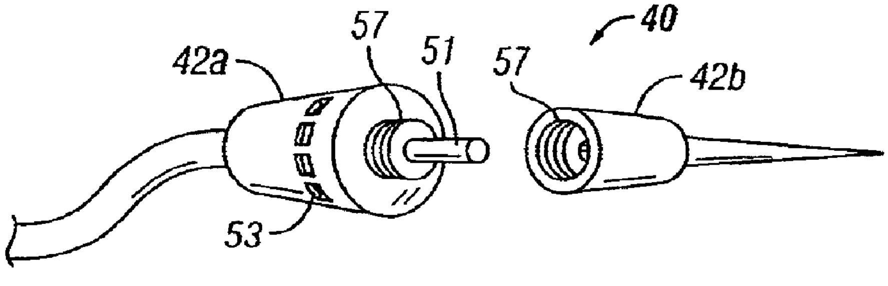
FIG. 5 is a perspective view of an alternative embodiment of the reducer of the present invention.

Another preferred embodiment of the reducer 40 is shown in FIG. 5. The housing 42 comprises two detachable components 42*a* and 42*b*. Component 42*a* defines the first cylinder 44 and component 42*b* defines the second cylinder 46. The first piston (not shown) is operably disposed within the first cylinder 44 and a rod 51 is integral with the first piston and extends distally therefrom. The second component 42*b* operably houses the second piston (not shown). The second component is preferably integral with a needle or catheter and contains a predetermined quantity of injectate which is packaged therewith. When the components 42*a* and 42*b* are connected, such as with the threaded connector 57 shown in the FIGURE, the distal end of the rod or plunger 51 abuts against the proximal side of the second piston, acting thereon during operation in the same manner as described above and shown in FIG. 4. Once the injectate has been administered, the needle may be removed from the patient and the second component 42*b* may be detached from component 42*a* and discarded. The first piston may be proximally withdrawn and the first component may be used again in conjunction with a new second component 42*b*. Though the rod 51 could be effectively integral with the proximal sidle of the second piston and abut against the first piston when components 42*a* and 42*b* are operably connected, this may result in accidental movement of the second piston while the second component 42*b* is being handled prior to use.

Figure 24:
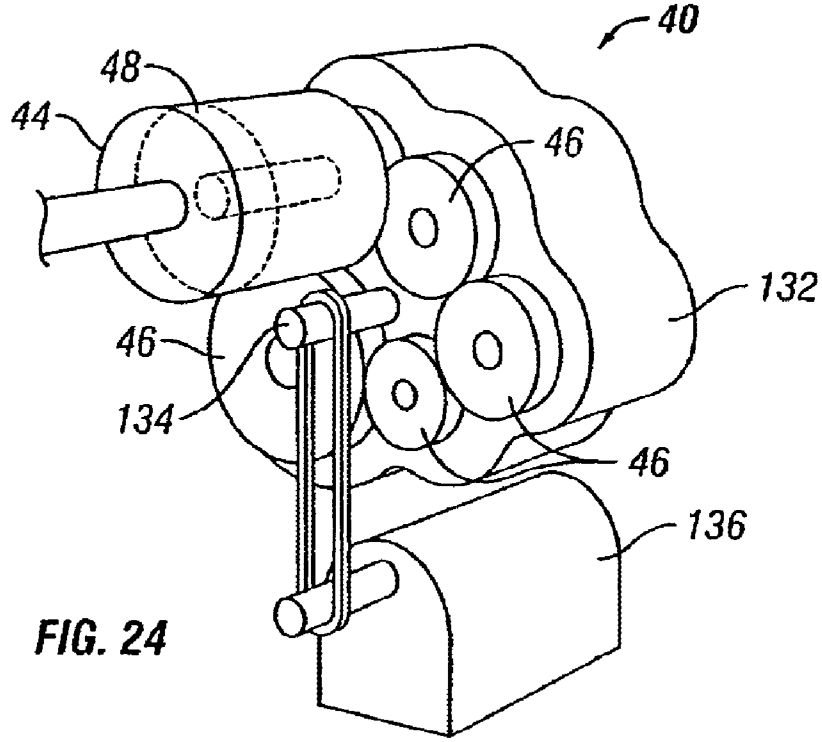
FIG. 24 is a perspective view of a preferred embodiment of the reducer of the present invention.

Yet another embodiment of the reducer 40 is shown in FIG. 24. The first cylinder 44 is provided which may be integral or an attachable to an automatic injection machine or syringe. A plurality of second cylinders 46, each having different diameters, are selectably indexable to become operatively associated with the first cylinder 44, giving a physician a wide range of reduction or amplification ratios to choose from. An indexing motor 136 may be associated with a rotatable or linearly moveable magazine 130 of second cylinders 46 such that software loaded into the automatic syringe may determine the appropriate second cylinder 46 for a given desired injection volume and flow rate. The embodiment shown provides a magazine 130 of second cylinders 46 each containing a piston (not shown) for interaction with the first piston 48 in the manner described above. The magazine 130 comprises a housing 132 which carries the second cylinders 46 and is rotatable around a pivot pin 134. This embodiment vastly increases the operating range of the automatic syringe device.

Figure 25:
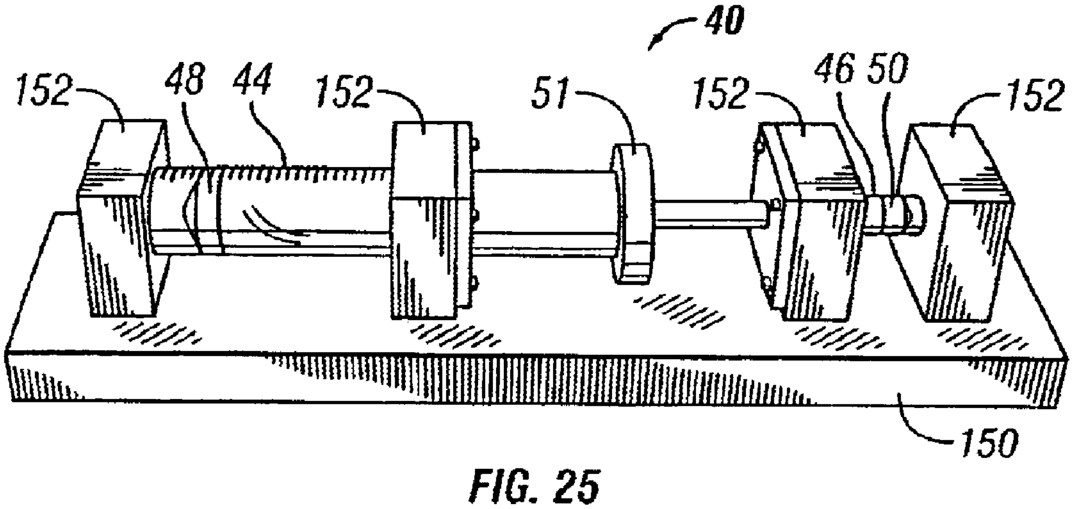
FIG. 25 is a perspective view of another preferred embodiment of the reducer of the present invention.

Still another embodiment of the reducer 40 is shown in FIG. 25. The first cylinder 44 and the second cylinder 46 are rigidly mounted to a base 150 via a plurality of mounting brackets 152. This arrangement fixes the first cylinder 44 relative to the second cylinder 46. The connecting rod 51 rigidly connects the first piston 48 to the second piston 50. The base plate 150 and mounting brackets 152 obviate a need for a vent to prevent a hydraulic lock as a housing is not necessary between the first cylinder 46 and the second cylinder 46.

The advantage of the reducer, when used manually, arises when the catheter attached to the proximal opening has a smaller diameter or cross section than that of the first chamber 44. This arrangement not only reduces the volume of injectate forced from the needle for a given volume of fluid introduced into the first chamber 44, it also reduces the linear distance the piston 48 or 50 moves compared to the distance a physician moves an input piston or syringe.

For example, assume the first chamber 44 has a cross-sectional area of $10^{-4}$ $m^2$, the second chamber 46 has a cross-sectional area of $10^{-5}$ $m^2$, and the catheter attached to the proximal opening 52 of the first chamber 44 also has a cross-sectional area of $10^{-5}$ $m^2$. Filling the catheter with a driving fluid and placing a syringe into the proximate end of the catheter for use in pushing fluid into the first chamber 44 will give the operating physician a great deal of control. If the physician pushes the syringe into the catheter 1 cm, there will be $10^{-7}$ $m^3$ or 0.1 ml of fluid injected into the first chamber 44. This will cause the first piston 48 to move $10^{-7}$ $m^3/10^{-4}$ $m^2=10^{-3}$ m or 1 mm. In other words, there is a linear reduction equal to the area of the input syringe divided by the area of the first piston 48, in this case, a 10 to 1 reduction.

Continuing with this example, the movement of the first piston 48 a distance of $10^{-3}$ m, which is equal to the movement of the second piston 50, causes the second piston 50 to force $(10^{-3}$ m$)(10^{-5}$ $m^2)=10^{-8}$ $m^3$ or 0.01 ml of injectate to exit the needle or catheter, a 10 to 1 reduction in volume injected. If two such reducers are connected in series, the reduction multiplies, becoming a 100 to 1 reduction.

This reducer 40 is particularly advantageous when used in conjunction with an automatic injection machine. These machines are expensive and only the most recent models are capable of measuring and delivering microinjections. The reducer 40 of the present invention allows both models to perform microinjections. This obviates the need to replace an expensive machine with an even more expensive machine.

These machines typically require an operator to enter a desired injectate volume into a computerized control board. The control board then calculates the linear distance that an automated piston should travel to force the desired volume of injectate or similar liquid through a catheter, and can do so with precise pressure control. However, with many machines, especially older models, there is a lower limit on the injectate volume that may be entered, making microinjections impossible. The reducer 40 makes microinjections with these machines possible.

Using the reducer 40 not only allows the machine to deliver smaller amounts of injectate than previously possible, it bifurcates the catheter into a hydraulic side feeding the first chamber 44 and an injectate side, downstream of the second chamber 46. This allows the use of water or similar, preferably incompressible and inexpensive, fluid to be used to force the expensive injectate into the patient.

Notably, that portion of the catheter between the patient and the reducer catheter must be filled with the desired injectate and free of air bubbles prior to operating the machine to avoid forcing gas bubbles into the recipient. A bleed valve 41 is preferably provided which is attached to the second chamber 46 for venting air therefrom. Additionally, a connection 43 may be provided so that a vial of medicament may be drawn from by the second piston 50. The connection 43 may be integral with or separate from bleed valve 41.

In addition to the weeping needles and reducers described above, it is also desired to be able to create a cloud of injectate or medicament in vivo. This cloud can be shaped to target a specifically shaped tumor or other spatial pattern, or provide a relatively uniform area of delivery of such injectates as steroids or local anesthetics. In order to create such a cloud, it may be desired to allow the injectate to flow from the needle at a higher rate such that a stream is produced, thereby propelling the injectate into the surrounding tissues. Attention is now directed to the remaining FIGURES which show just a few of the envisioned arrangements.

Figure 6:
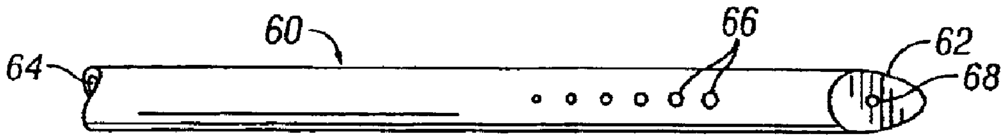
FIG. 6 is a side elevation of an elongate member of the present invention.

FIG. 6 shows an elongate member 60 having a sharpened tip 62 at its distal end and defining a central lumen 64 and a plurality of holes 66 extending through the side wall of the member 60 to the central lumen 64. The sharpened tip 62 is shown as defining a small end hole 68 extending through to the central lumen 64, but could have more open, or could be closed depending on the desired cloud shape. It is understood that the components and holes of the present embodiments could be any size suitable to the intended uses. End holes 68 having diameters on the order of 0.002–0.008" have been particularly effective.

It can be seen that holes 66 increase in diameter toward the distal end. This creates a pressure gradient which results in a relatively uniform cloud shape. As injectate is forced through the needle-like member 60, a pressure drop is felt across each hole 66 as some of the injectate is lost. Increasing the size of the holes 66 in relation to their proximally adjacent neighboring holes 66 accounts for this pressure drop and maintains a relatively constant flow rate by increasing the size of the stream through each subsequent hole 66. On the other hand, if it is desired to create a cloud which has a larger proximal end and a smaller distal end, holes 66 of a relatively uniform diameter can be used. Altering the size, shape, density, angle of drilling will permit any arbitrary shape of injectate deposition.

Figure 7:
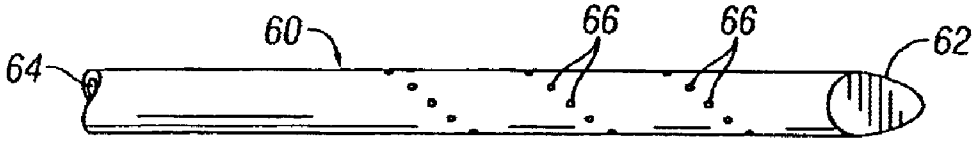
FIG. 7 is a side elevation of an alternative elongate member of the present invention.
Figure 20:
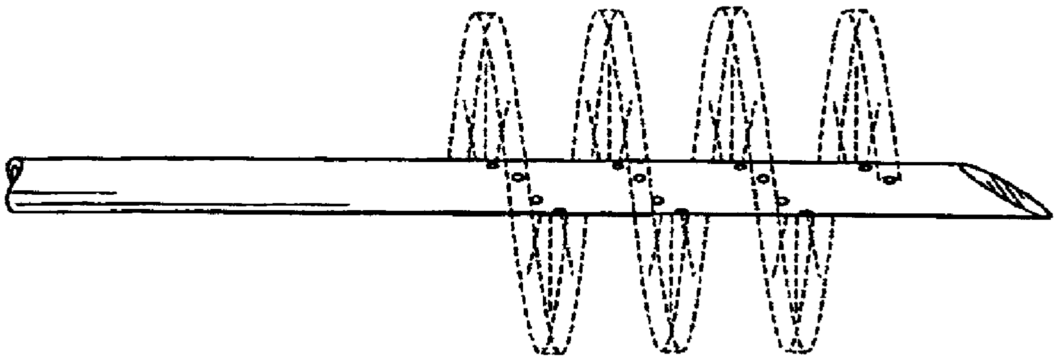
FIG. 20 is a side elevation view of a needle having holes constructed and arranged to form a spiral ribbon cloud pattern.

FIG. 7 shows an elongate member 60 having a closed tip 62 and a plurality of holes 66 which are positioned to wrap around the member 60 to form a spiral. Like all of the holes 66, they lead into the central lumen 64. The resulting cloud shape formed when using this embodiment of the elongate member 60 is a helical ribbon. An example of a cloud having a ribbon shape is shown in FIG. 20. Positive results have been obtained using 23 and 25.5 gauge needles having spaces between the holes 66 of approximately 0.01". This shape has been combined with one or more end holes 68 of 0.0047".

Figure 8:
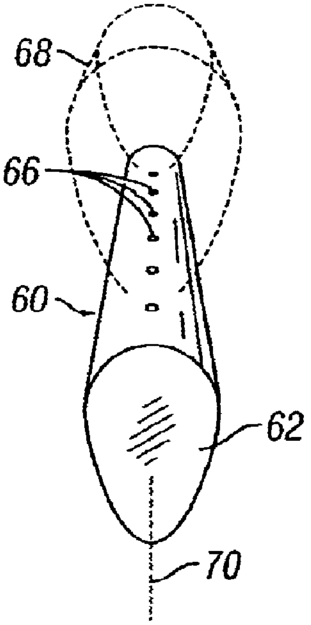
FIG. 8 is a front perspective view of an elongate member of the present invention producing a shaped injectate cloud.
Figure 9:
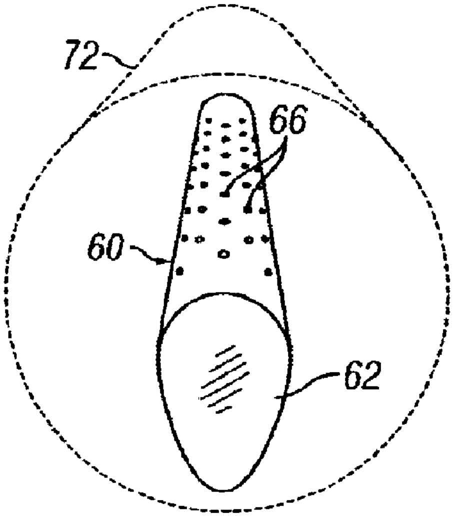
FIG. 9 is a front perspective view of an elongate member of the present invention producing an alternatively shaped injectate cloud.

FIGS. 8 and 9 show diagrammatic depictions of resulting cloud shapes for respectively given hole patterns. The hole pattern in FIG. 8 is a single line of holes 66 extending down one side of the member 60. The holes 66 increase in diameter as they approach the tip 62 in order to create a relatively uniform flow rate through each hole. The resulting cloud shape is roughly a cylinder, shown in FIG. 8 in phantom lines and given the number 68 for clarity. It can be seen that the cloud 68 has a central axis which is roughly parallel to but laterally offset from the central axis 70 of the member 60.

FIG. 9 shows another cloud shape or pattern 72. The holes 66 in the member 60 are, again, increasing in diameter as they approach the distal tip 62. However, these holes 66 are constructed and arranged in a relatively uniform pattern around side wall of the member 60. The cloud pattern 72 results in a cylinder which is relatively concentric with the member 60.

Figure 10:
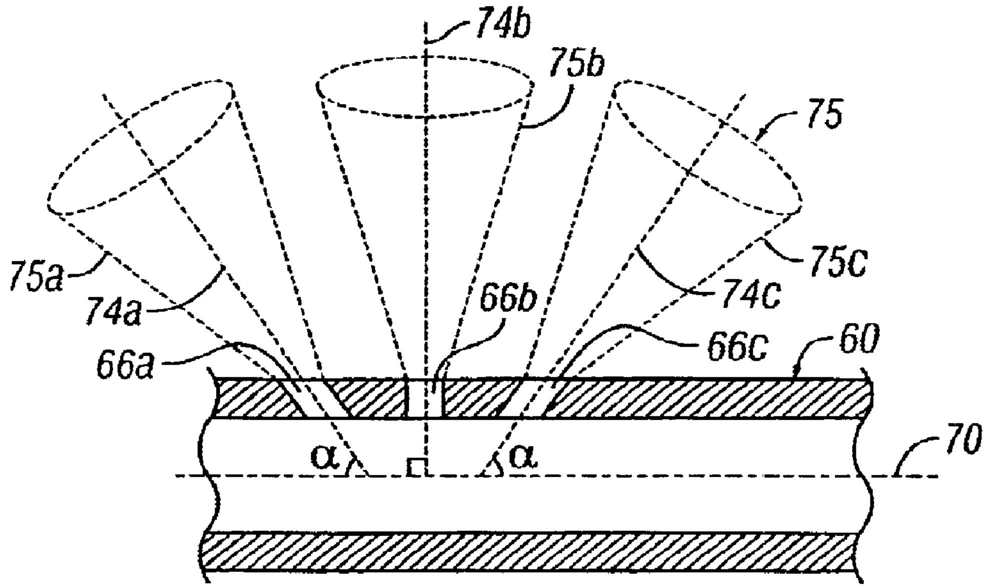
FIG. 10 is a sectional side elevation of a portion of an elongate member showing a distally, perpendicularly and proximally angled holes leading from the central lumen of the member, whereby the direction of holes diffuse the injectate in space, within the desired pattern.

It is now clear to one skilled in the art that an infinite number of cloud patterns can be achieved by following the teachings of the present invention and varying the size and locations of the holes 66 along the length of the member 60. For example, if it is desired to project a cloud of injectate in a distal or proximal direction, relative to the placement of the hole 66 from which the cloud is being projected, the hole 66 may be formed in the member 60 such that it has a central axis 74 which forms an acute or obtuse angle $\alpha$ to the central axis 70 of the member 60. FIG. 10 shows such a configuration. The cloud 75 created is somewhat conical as it is created by a single hole 66. As seen in FIG. 10, it may be possible to create a large cloud with a relatively short member 60 by combining holes 66 having axes 74*a* and 74*c* with obtuse and acute angles a to the central axis 70 with a hole 66*b* having an axis 74*b* which is perpendicular to the central axis 70. The resulting clouds 75*a*, 75*b*, and 75*c* combine to create a cloud 75 which is large given the relatively close proximity of the holes 66*a*, 66*b* and 66*c*.

Figure 21:
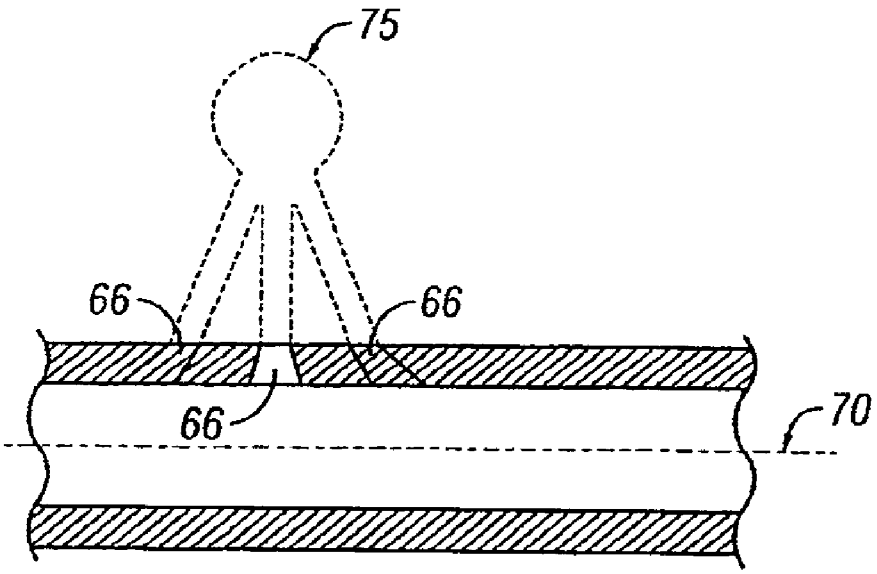
FIG. 21 is a sectional side elevation of a portion of an elongate member showing a distally, perpendicularly and proximally angled holes leading from the central lumen of the member, whereby the direction of holes concentrate the injectate in space, within the desired pattern.
Figure 22:
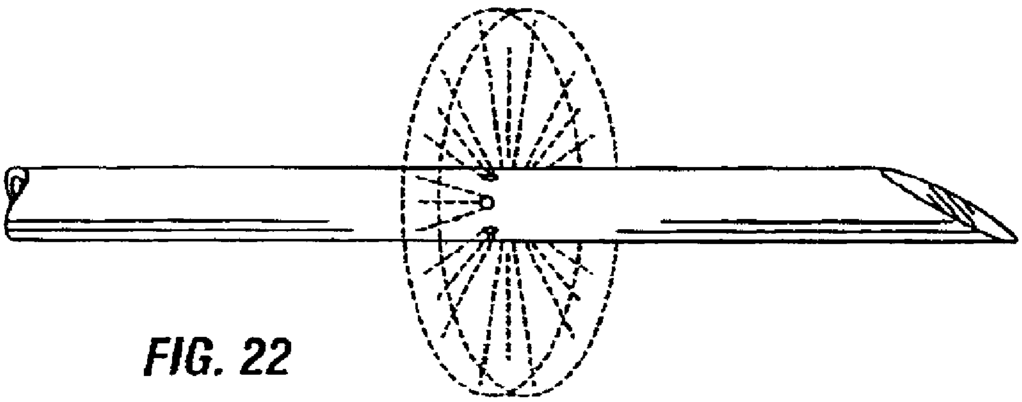
FIG. 22 is a side elevation of a needle having holes constructed and arranged to form a cloud in the shape of a disk.
Figure 23:
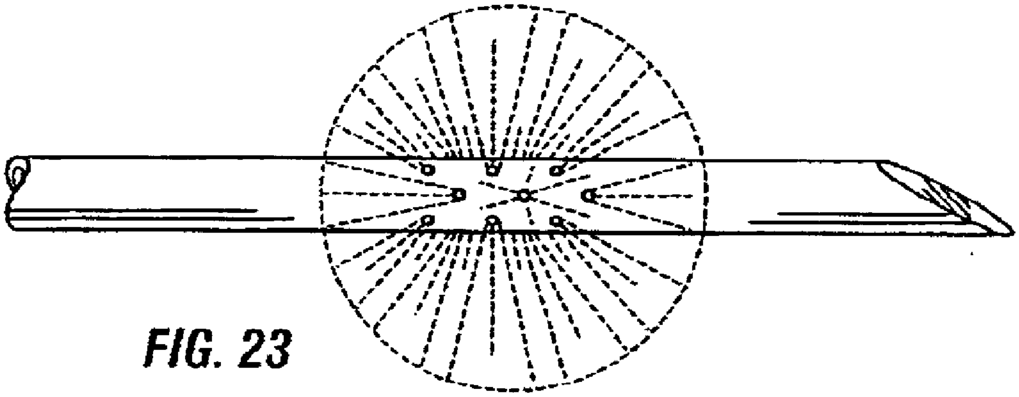
FIG. 23 is a side elevation of a needle having holes constructed and arranged to form a cloud in the shape of a sphere.

Alternatively, it may be desired to focus more than one stream of injectate at a common target site, thereby increasing the concentration of injectate at the site. FIG. 21 shows three holes 66 angled such that their streams are aimed to converge on a specific target site, thereby forming a very concentrated cloud of injectate 75. Notably, the holes 66 may be shaped to focus, or diffuse, more efficiently by tapering the sides of the holes such that the diameter of the hole increases or decreases as it extends from the inner lumen to the outer surface of the needle or catheter.

More versatility is achieved when the member 60 is coupled with a flow manipulating device such as a sheath or a stylet. FIGS. 11–16 show various embodiments where the flow from member 60 is can be altered during use by the use of such a flow manipulating device.

Figure 11:
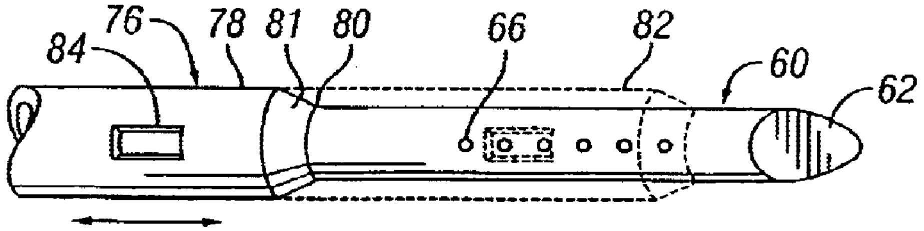
FIG. 11 is a side elevation of a preferred embodiment of the present invention.

FIG. 11 depicts a sharpened member 60 which has a sheath 76 slideably disposed over the member 60. The inner dimensions of the sheath 76 closely match the outer dimensions of the member 60 such that when the sheath 76 over one of the holes 66, the hole is occluded and substantially no injectate is allowed to flow therefrom. It can be seen that sheath 76 is slideable from a proximal position 78, whereby an open distal end 80 of the sheath 76 is proximally displaced from the holes 66, to a distal position 82 whereby the distal end 80 is distally displaced from the most distal hole 66. Preferably, the open distal end 80 is defined by a tapered section 81, thereby preventing damage to surrounding tissue when the sheath 76 is slid distally. If a solid sheath 76 is used, all of the holes 66 will by occluded when the sheath 76 is in the distal position 82. Alternatively, as is shown in FIG. 11, one or more openings 84 may be defined by the sheath 76. The opening 84 may be sized to allow fluid to flow from a predetermined number of holes 66 while some or all of the other holes 66 remain occluded.

Figure 12:
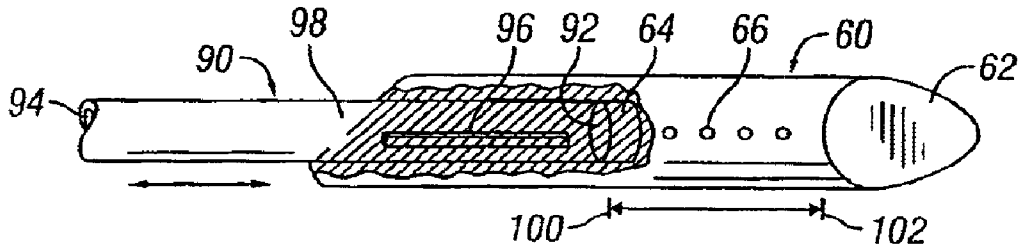
FIG. 12 is a side elevation of a preferred embodiment of the present invention whereby part of the elongate member is cut away to show the detail of the stylet.

FIG. 12 shows an alternative embodiment wherein two pieces are used in combination to manipulate flow patterns during use. Member 60 has a closed sharpened tip 62 and a plurality of holes 66. A stylet 90 is slideably received within the central lumen 64 of the member 60. The stylet 90 comprises a distal end 92 and its own inner lumen 94 through which fluid may be introduced to the elongate member 60. The stylet 90 also comprises at least one opening 96 defined either by its side wall 98 or by its distal end 92. An elongate opening 96 extends relatively parallel to the central axis of the stylet 90. Again, the stylet 90, like the aforementioned sheath 76, is moveable from a proximal position 100 to a distal position 102. In the proximal position 100, the distal end 92 of the stylet 90 is proximally displaced from the distal most hole 66. In the distal position 102, the distal end 92 of the stylet 90 is distally displaced from the distal most hole 66. Moving the stylet 90 from the proximal position 100 to the distal position 102 will have widely varying effects on the resulting cloud shape based on the position, size, and shape of the opening 96. This will be demonstrated in more detail below.

The stylet 90 has an outer diameter which is substantially equal to the inner diameter of the central lumen 64 of the elongate member 60. This ensures that fluid does not leak from the opening 96 until the opening 96 is in line with one of the plurality of holes 66. Looking at FIG. 12, given the shape and size of the opening 96 and the locations of the holes 66, it can be seen that when the stylet 90 is in the proximal position 100, the elongate opening 96 is proximally displaced from the hole 66 so that no fluid is allowed to flow therethrough. As the stylet 90 is advanced from the proximal position 100 to the distal position 102, the elongate opening 96 begins to uncover the plurality of holes 66 and a cloud shape begins to result. The cloud grows in length distally as the stylet 90 is advanced until the stylet 90 achieves the distal position 102 whereby all of the plurality of holes 66 are uncovered and emitting fluid or injectate.

Figure 13:
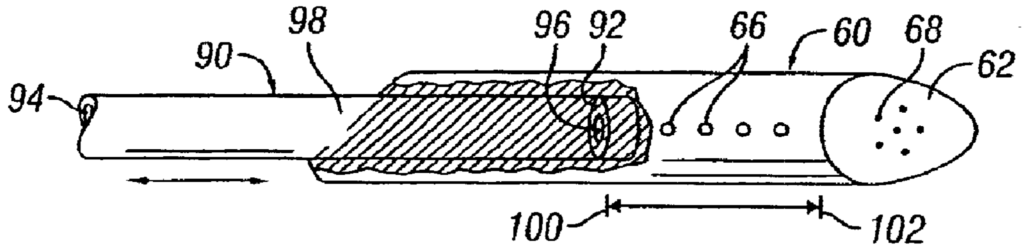
FIG. 13 is a side elevation of a preferred embodiment of the present invention whereby part of the elongate member is cut away to show the detail of the stylet.

FIG. 13 shows a different arrangement which will have a drastically different effect. It can be seen that the stylet 90 of this embodiment defines no holes in the side wall 98, but that the central lumen 94 passes through the stylet to an opening 96 in the distal end 92. In this arrangement, when the stylet 90 is in the proximal position 100, whereby the distal end 92 is proximally displaced from the proximal most hole 66, fluid is allowed to flow through the stylet 90 and all of the plurality of holes 66. As the stylet is advanced to the distal position 102, the holes become occluded by the side wall 98 of the stylet 90. Once the stylet 90 achieves the distal position 102, all of the plurality of holes 66 are covered or occluded. FIG. 13 shows an embodiment, similarly shown in FIG. 6, where distal openings 68 may be defined by the elongate member 60. Therefore, when the stylet 90 achieves the distal position 102, fluid is still allowed to pass through the hole 68. However, if it is desired to prevent all fluid from flowing through elongate member 60 when the stylet has achieved the distal position 102, the sharpened tip 62 may be solid so that the stylet 90 would not allow any fluid to flow through the elongate member 60 when it achieves the distal position 102.

Some configurations, such as that shown in FIG. 12, require that the shaped opening 96 is aligned with the plurality of holes 66. In other words, if the stylet were to be rotated in one direction or another, the elongate opening 96 may not align with any of the plurality of holes 66 and therefore would not function. It may be desired to provide a key 100 which protrudes from the side wall 98 of the stylet 90 and aligns with a slot 102 defined by the elongate member 60. Alternatively, it may be desired to controllably allow both longitudinal and rotational relative movement between the member 60 and the stylet 90 or sheath 76. To provide more control, a frictional threading (not shown) may be provided between the two.

Figure 15:
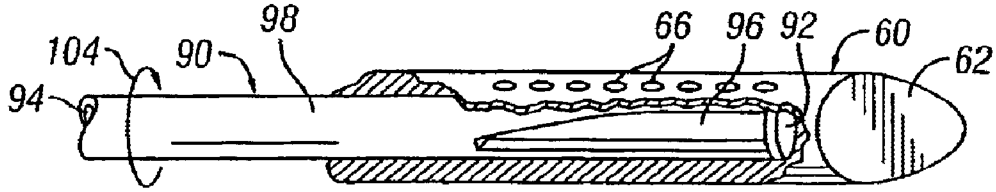
FIG. 15 is a side elevation of a preferred embodiment of the present invention whereby part of the elongate member is cut away to show the detail of the stylet.
Figure 16:
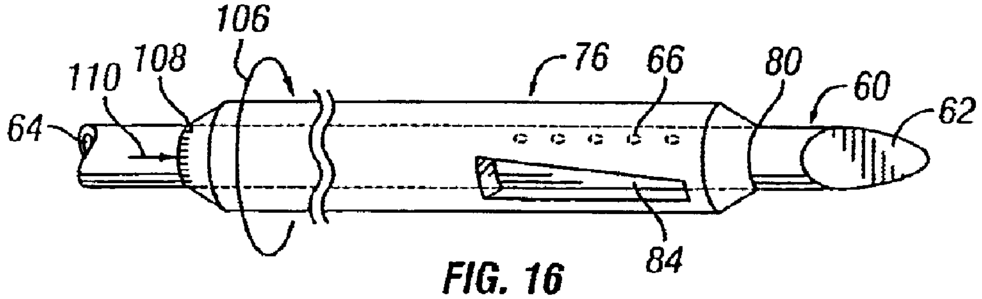
FIG. 16 is a side elevation of a preferred embodiment of the present invention whereby a rotatably sheath is operably disposed over the elongate member.

FIGS. 15 and 16 show how a twisting motion of stylet 90 can be used advantageously. FIG. 15 shows a stylet 90 having an opening 96 defined by its side wall 98 which increases in width toward its distal end 92. When used with an elongate member 60 having a line of holes 66, the stylet 90 can be twisted to increase the number of holes 66 that become aligned with the opening 96. This stylet 90 may operably remain in a most distal position, as shown. The stylet 90 is shown in a position whereby the opening 96 is angularly displaced from the plurality of holes 66. However, if the stylet were rotated in a direction as indicated by arrow 104, the distal most hole 66 would be the first to be opened followed quickly by the adjacent holes in a proximal direction until all of the holes 66 were open. This configuration gives a physician a great deal of control as to the number of holes 66 that are allowed to emit injectate.

Figure 14:
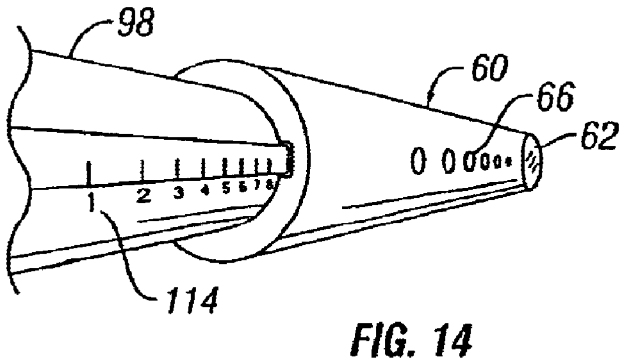
FIG. 14 is a perspective view of a key of the present invention.

FIG. 16 shows how this twisting arrangement may be incorporated on an elongate member-sheath configuration as was described above. It can be seen that an elongate member 60 is provided with a sharpened tip 62 and a sheath 76 rotatably disposed thereon. Sheath 76 defines an opening 84 which has a wider proximal end and a narrower distal end. A plurality of holes 66 is shown in phantom beneath the sheath 76. As the sheath 76 is rotated relative to the member 60 in a direction as indicated by arrow 106, the opening 84 begins to uncover the holes 66 starting with the proximate-most hole and eventually uncovering all of the holes 66. Indicator marks 108 are shown at the proximal end of the sheath 76. The indicator marks 108, used in conjunction with a position arrow 110, indicate to the physician how many holes 66 are uncovered. A similar indicator 114 is shown in FIG. 14 which is configured for one of the sliding embodiments shown herein. The markings on the stylet 98 indicate the number of holes 66 which remain open or closed, depending on the configuration of the stylet 98. Alternatively, it is envisioned to provide radiopaque markers (not shown) on the needle itself such that the needle could be visualized and its position ascertained in vivo.

One skilled in the art will quickly realize that the flexibility provided by various shaped opening and variously placed holes 66 will allow an infinite number of variations in order to achieve any desired cloud shape or sequence of hole uncoverings as one member is slid or rotated against another member to uncover or occlude desired holes.

Figure 17:
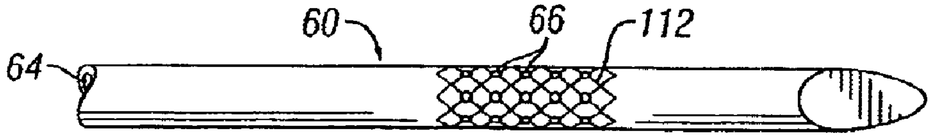
FIG. 17 is an embodiment of the elongate member of the present invention having scored marks thereon.

One problem which has not been addressed involves back pressure caused by adjacent tissue into which fluid is being injected. This is especially cumbersome at low injection flow rates. In order to provide more space for injectate to flow, thereby reducing back pressure, scoring 112 may be provided on the outer surface of the elongate member 60 adjacent the holes 66. This is seen in FIG. 17.

Figure 18:
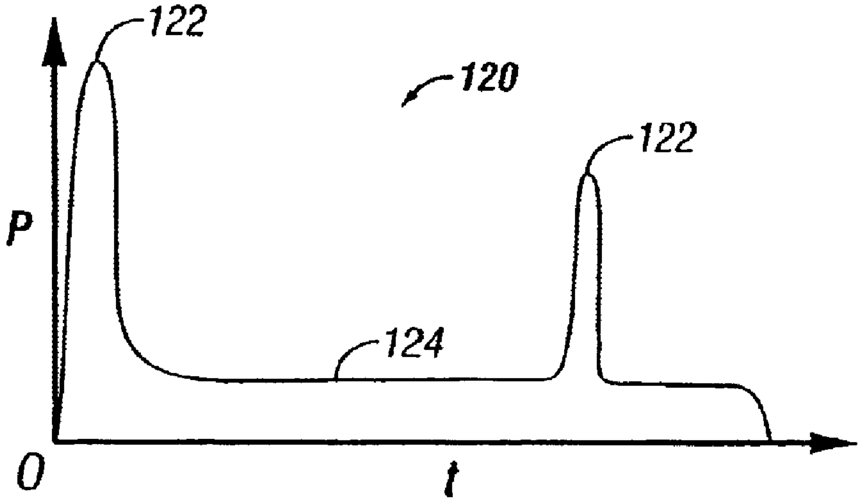
FIG. 18 is a pressure versus time graph of a preferred pressure waveform of the present invention.
Figure 19:
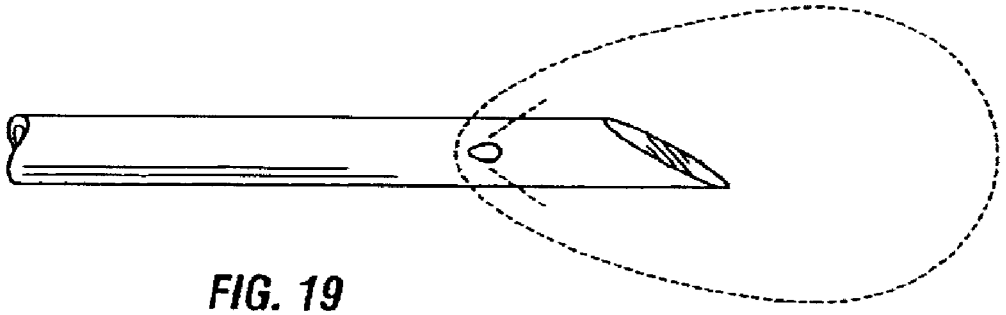
FIG. 19 is a side elevation view of a needle having holes constructed and arranged to form a tear drop cloud pattern.

FIG. 18 shows a graph of a pressure waveform 120 which may be used to further enhance the perfusion of an injectate into a fibrous tissue such as the myocardium. An initial pressure spike 122 is provided which is of sufficient force, such as 50 to 300 mmHg but not limited thereto, to pretreat or prepare the tissue for injectate reception. In other words, the hydraulic pressure of fluid exiting from the needle will locally raise the tissue pressure where the needle holes are located. By controlling the pressure of the needle, tissue pressure can be controlled. This is important because tissue pressure may be used to determine where the injectate flows into the tissue. For example, a rapid increase in myocardial tissue may separate the muscle bundles from the connective stromal tissue, so that fluid flows selectively into the interstitial regions rather than the cellular areas. The waveform 120, having at least one spike 122 followed by a lower pressure level 124, can create such an effect. It may be desired to provide a subsequent spike 122, as shown, to reopen or separate the muscle bundles if necessary.

Figure 26:
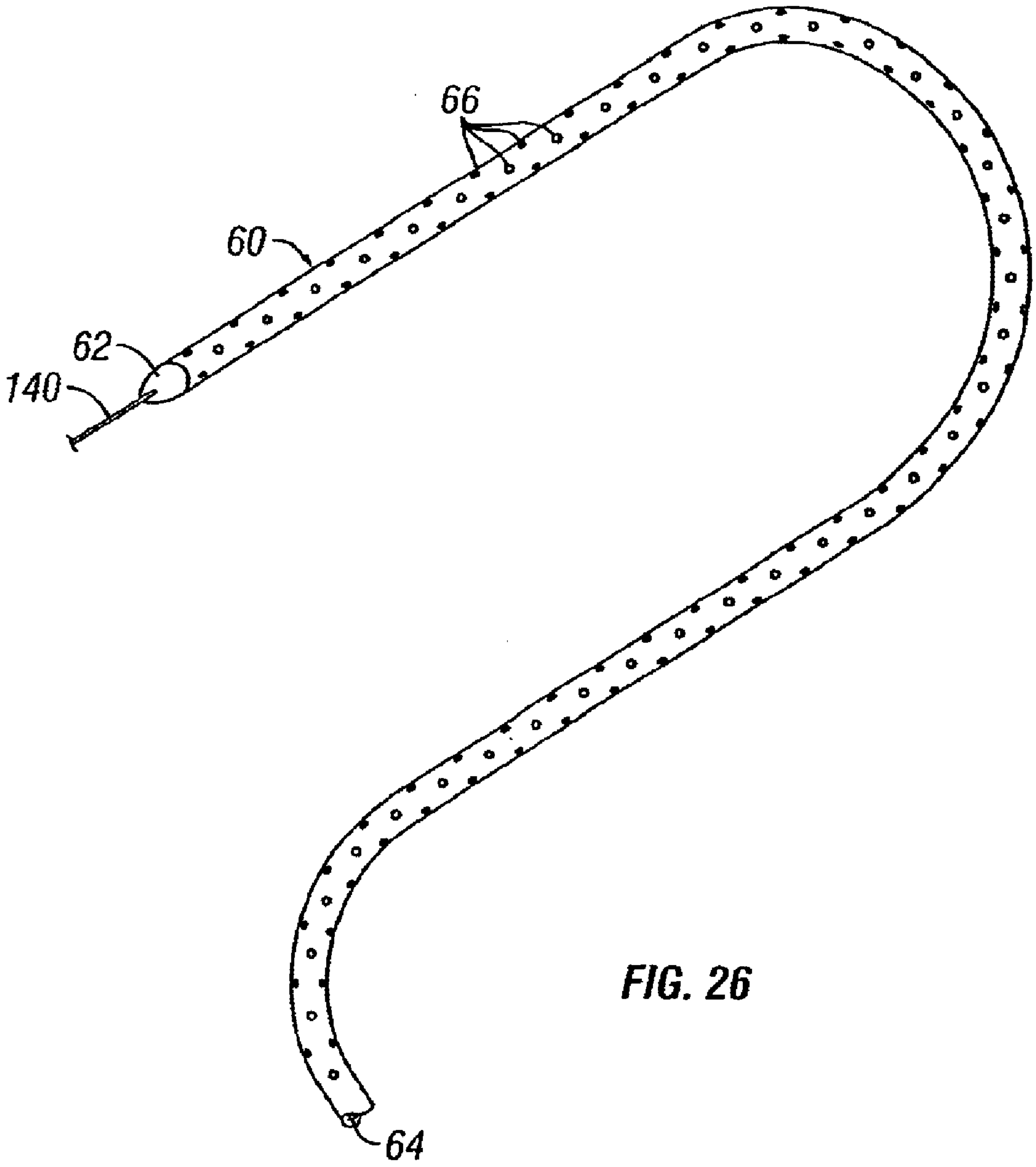
FIG. 26 is a preferred embodiment of a catheter of the present invention.

It is noted that, though the various embodiments described above place an emphasis on the use of a needle at the distal end of the devices, the various principles taught herein also apply to a catheter without a needle. Thus, the term elongate member 60 has been used to encompass needles, catheters, and similar lumen-defining elongate devices suitable for use in the body. A specific example of an elongate member 60 without a needle is shown in FIG. 26. Provided is a flexible, catheter-style elongate member 60 comprising a generally conical or somewhat pointed tip 62 at its distal end and defining a central lumen 64 and a plurality of holes 66 extending through the side wall of the member 60 to the central lumen 64. The tip may or may not include a small hole 66.

In a preferred embodiment, the tip 62 is constructed of a soft durometer plastic which accommodates a guidewire 140 passing therethrough. The plastic is chosen such that when the member 60 is in a desired position, the guidewire 140 may be removed and the plastic seals itself, thereby leaving a substantially solid tip 62.

Also shown in FIG. 26 is an embodiment whereby the elongate member 60 is a catheter or similar device of substantial length, such as between 10 and 70 centimeters, or any length suitable for use in vivo, with holes 66 occurring over substantially the entire length. Such an embodiment is particularly useful for operations involve blood clots in longer blood vessels such as those found in the legs.

In a related embodiment, the invention method comprises inserting the distal portion of the invention needle into an interior body wall or tissue of the subject and applying sufficient pressure to a liquid medicament in fluid communication with the distal portion of the needle to expel a therapeutic amount of the medicament such that the medicament weeps multidirectionally from the pores in the distal portion thereof into the interior body wall or tissue without substantial leakage or loss of the medicament at the surface of the body wall. The body wall can be located within a natural body cavity or any opening.

The invention method utilizing the needle with weeping tip is particularly useful for injection of medicaments into the wall of an interior organ that is subject to motion during the injection procedure, for example, the wall of a beating heart of adjacent arterial walls during electrophysiologic testing, transmyocardial revascularization, and the like. Additional internal organs subject to movement into which injections can be made using the invention methods include the stomach, esophagus, gallbladder, liver, bowel, kidney, lung, and the like.

The embodiment utilizing a weeping, or porous needle is more thoroughly described in U.S. patent application Ser. No. 09/468,689, filed Dec. 20, 1999 and Ser. No. 09/829,022, filed Apr. 9, 2001, and is incorporated by reference herein.

Furthermore, in order to determine if a multi-holed needle would better distribute the angiogenic factors, the flow patterns of the diffusionary needle have been analyzed and the findings used to develop a method for determining the optimal design given experimentally defined flow velocities. The optimal design for angiogenic applications involves a constant flow of angiogenic fluid along the porous length of the needle, thereby providing an even factor distribution.

Multiple holes on the shaft of the needle proved effective in improving the distribution of the injectate (a contrast agent was used for analysis purposes) but had shortcomings in that the holes did not deliver the material equally to the area around the holed section of the needle. A conclusion was made that this was due to at least two problems: a small and uneven distribution of holes on the shaft of the needle and an unequal flow through the holes on the needle depending on their relative locations. A mathematical analysis was performed to determine the validity of this conclusion.

The analysis applied to a needle having a closed distal end and holes located only along the shaft near the distal end of the needle. Generally, a pressure drop through any constant inner diameter tube is characterized by Poiseuille's equation:

$$\frac{dP}{dx} = -\frac{128\,\mu Q}{\pi d^4} \tag{1}$$

where P is pressure, x is the distance along the holed section of the needle, $\mu$ is viscosity, Q is flow, and d is the inner diameter of the tube or needle. Additionally, because the tube is porous, flow constantly decreases down the porous or holed section of the tube. Assuming that the holes on the side of the tube are arranged in such a manner that the porous section is equally porous along the entire length, the pressure drop through the porous tube becomes:

$$\frac{dP}{dx} = -\frac{128\,\mu Q}{\pi d^4}\left(1 - \frac{x}{l}\right) \tag{2}$$

wherein l is the length of the porous section of the needle. Pressure, as a function of distance, x, becomes:

$$\int_{P_o}^{P} dP = -\frac{128\,\mu Q}{\pi d^4}\int_0^x \left(1 - \frac{x}{l}\right)dx \tag{3}$$

$$\Rightarrow P(x) = P_o - \frac{128\,\mu Q}{\pi d^4}\left(x - \frac{x^2}{2l}\right) \tag{4}$$

Equation 4 then gives the pressure drop along the porous section of a tube, or the section of the needle with holes along the shaft. Assuming that the flow from the porous section of the needle is constant and equal along the length, l, of the porous section, the velocity, v, of the fluid flowing out of the hole can be calculated using Torricelli's formula, which is Bernoulli's equation simplified to apply to a draining tank:

$$v = C_{viscous}\sqrt{2gH} \tag{5}$$

where $C_{viscous}$ is a coefficient accounting for frictional losses, g is gravity, and H is the height of the draining tank. This draining tank formula can be manipulated to apply to fluid being forced through a needle by acknowledging that:

$$P = \rho gH \text{ or } gH = \frac{P}{\rho} \tag{6}$$

so that the velocity, v, of flow through a hole can be represented by:

$$v = C_{viscous}\sqrt{\frac{2P}{\rho}}. \tag{7}$$

Knowing the velocity, v, of fluid flowing through a hole, the flow rate, q, through a cross-section of porous material, such as that of the needle, is calculated as:

$$q = C_{contraction} vA \text{ or } q = C_{contraction} v(n\pi r^2) \tag{8}$$

where q is cross-sectional flow, A is the area of the hole(s), n is the number of holes at the particular cross-section (number of holes per unit length), r is the radius of the hole(s), and $C_{contraction}$ is a contraction coefficient account for a fluid jet's tendency to contract or curve from the sharp orifice, or hole edge.

The cross-sectional flow, q, then becomes:

$$q = C_{contraction} C_{viscous}\sqrt{\frac{2P}{\rho}}(n\pi r^2). \tag{9}$$

One can define a discharge coefficient $C_{discharge}$ as the product of the $C_{contraction}$ and $C_{viscous}$.

Assuming that flow from the needle at any given cross-sectional area is constant throughout the length of the holed portion of the needle, then:

$$ql = Q \tag{10}$$

Rearranging and combining Equations 7, 9, and 10 provides:

$$n = \frac{Q}{\pi r^2 l C_{discharge}\sqrt{\frac{2P}{\rho}}} \tag{11}$$

In so far as pressure, P, has been defined as a function of distance in Equation 4, the number of holes, n, as a function of distance for a desired flow rate can be represented by:

$$n(x) = \frac{Q}{\pi r^2 l C_{discharge}\sqrt{\frac{2\left[P_o - \frac{128\mu Q}{\pi d^4}\left(x - \frac{x^2}{2l}\right)\right]}{\rho}}} \tag{12}$$

Equation 9 then gives the concentration of holes at positions along the porous section of the needle needed to obtain constant and equal flow along the entire holed portion of the needle. An alternative method of obtaining this equal and constant flow is to keep hole concentration constant and just change the size of the holes as a function of position. Simply rearranging Equation 9 and solving for radius, r, as a function of distance provides:

$$r(x) = \frac{Q}{n\pi l C_{discharge}\sqrt{\frac{2\left[P_o - \frac{128\mu Q}{\pi d^4}\left(x - \frac{x^2}{2l}\right)\right]}{\rho}}}. \tag{13}$$

Thus, it is shown that the net exit of injectate as a function of length along the needle can be controlled by varying the size of holes or by utilizing a differing density of the same sized hole along the length of the needle/catheter. This variation in hole density can create any pattern of injectate also, as previously disclosed. Such a pattern of hole density can be used primarily to cause a constant injectate per unit of needle length. With additional variations, the pattern can be adjusted to create any desired injectate pattern around the needle. The outcome of this design is to permit concentration control of the injectate.

The mathematical findings were applied to a specific embodiment of the present invention in order to obtain the following results:

The specific embodiment used a flow rate, Q, of 1.5 $cm^3/s$, an inner diameter, d, of 0.04064 cm, which is the inner diameter of a 22-gauge needle, and porous length, l, of 1 cm. Given the low molecular weight of proteins and genes suspended in saline solution, viscosity, $\mu$, and density, $\rho$, of the angiogenic fluid was approximated to that of water at 40° C. The hole radius, r, was set at 25 microns, which is the lower limit of the hole size that a laser can create. This hole size was selected because it represents the lower limit and, therefore, larger pressures would be needed to force the same amount of fluid through it, thereby creating larger maximum velocities through the holes. The viscous coefficient, $C_{viscous}$, which accounts for frictional losses was assumed to be 0.95, a 5% loss. The contraction coefficient, $C_{contract}$, for a sharp edged orifice is 0.61, therefore the discharge coefficient, $C_{discharge}$, is 0.58.

The ideal design or placement of the optimal number of holes in the optimal position is dependent on the desired maximum velocity leaving the holes. It is clear, from equations 4 and 7, that the pressure before the beginning of the porous section of the needle, $P_o$, will be determined by the desired velocity, v. $P_o$ is then related to the pressure at the pump required to generate this ideal velocity for a given flow rate by Poiseuille's law. The linear pressure drop along the catheter, although small because of the small diameter of the catheter, must be taken into account when programming into the power injector.

Figure 27:
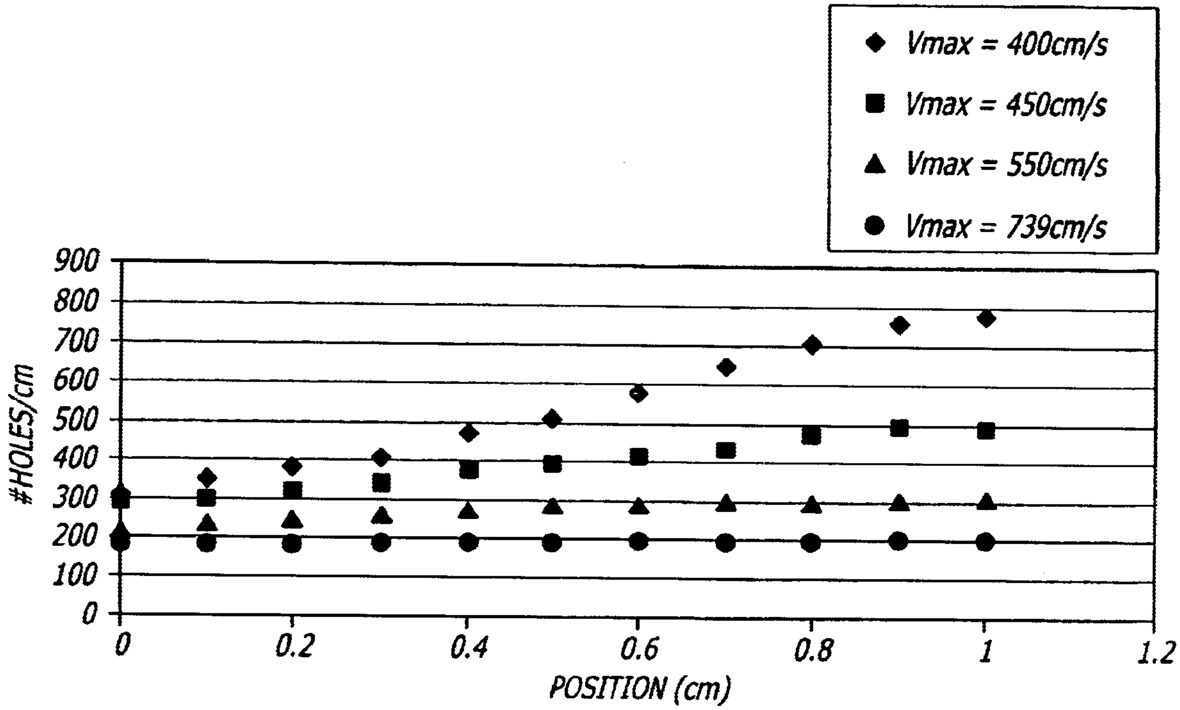
FIG. 27 is a first plot showing flow characteristics useful for implementing the present invention.

FIG. 27 shows the number of holes per centimeter at one-millimeter intervals along the length of the porous section of the needle for four different maximum velocities. This plot is an example of a determination of the optimal design for four given values of Vmax.

An additional consideration when designing the optimal needle is that if the pressure is too low, the number of holes required to maintain constant flow may exceed the number of holes that can fit on the needle without creating the risk that the needle could break off in the patient. In order to maintain the structural integrity of the needle, the porosity is kept under 20%. By requiring two diameters of steel for every 1 hole diameter, the geometric maximum number of holes per centimeter for a 22-gauge needle with 50 micron diameter holes is 560. Looking at FIG. 27 Vmax=400 cm/s exceeds the geometric limit and therefore cannot be considered a viable design.

Figure 28:
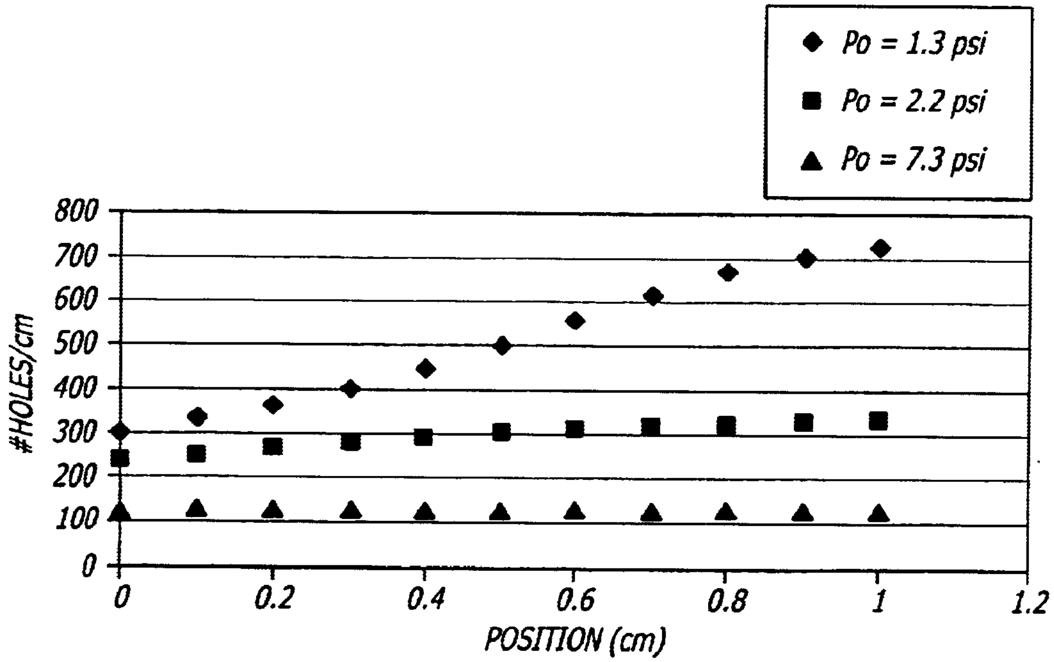
FIG. 28 is a second plot showing flow characteristics useful for implementing the present invention; and, FIG. 29 is a third plot showing flow characteristics useful for implementing the present invention.

FIG. 28 shows that if pressure exceeds 7.3 psi, the number of holes per centimeter not only decreases, but becomes constant over the length of the porous section.

Recalling Equation 13, hole arrangement or concentration as a function of position could be held constant and hole size could be varied. Though manufacturing costs may decrease if hole size is kept constant, as shown above, there are many embodiments where hole location is crucial, such as those involving strategic occlusion.

Figure 29:
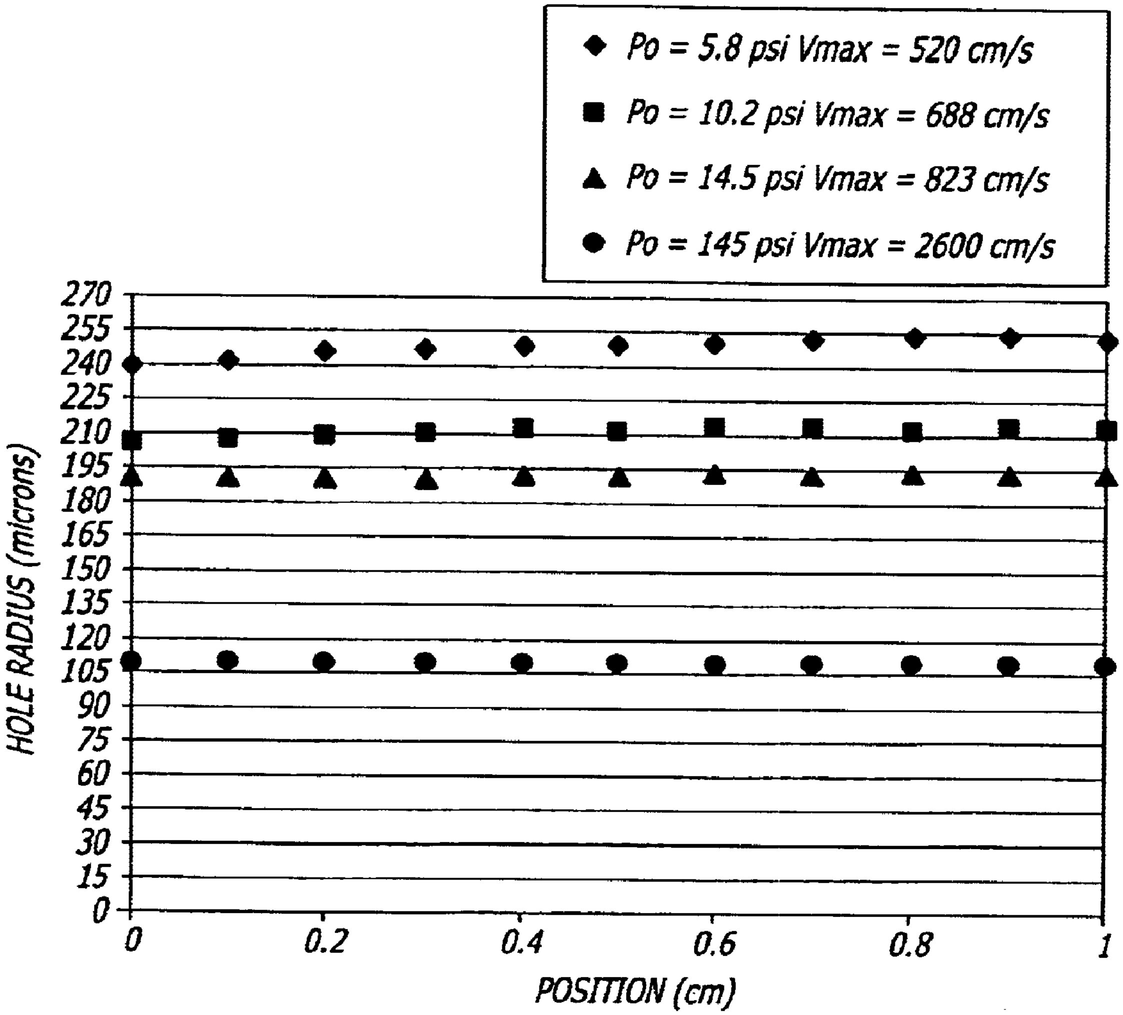

Therefore, using Equation 13 and keeping the remaining variables the same, the number of holes per centimeter is fixed, for purposes of this analysis, at 160. The results, though more difficult to notice, show that an increase in radius of the hole size is necessary to maintain constant flow, as shows in FIG. 29. As was the case above, when the number of holes varied, FIG. 29 shows that increasing the pressure beyond a value of 145 psi produces a constant radius of holes. Again geometric constraints must be considered.

While the invention has been described in detail with reference to certain preferred embodiments thereof, it will be understood that modifications and variations are within the spirit and scope of that which is described and claimed.

What is claimed is:

1. A medical device for dispensing injectate, in a predetermined shape, size and concentration, the device comprising:

an elongate member having a side wall defining a central lumen and having a distal end and a proximal end, the proximal end operably attachable to an injectate-providing catheter such that said catheter is in fluid communication with said lumen;

a plurality of holes defined by said side wall and extending from said lumen to an exterior of said side wall;

said plurality of holes having a preset distribution pattern, a preset diameter and a preset axis of orientation relative to an axis of said central lumen so as to form a predetermined specific shape of injectate adjacent said lumen, said preset distribution pattern being one straight line of holes parallel to a longitudinal axis of said lumen;

said preset diameter of each of said plurality of holes progressively increasing in a direction towards said distal end of said elongated member;

said preset axis of orientation being substantially perpendicular to said longitudinal axis of said lumen;

said predetermined shape of injectate being a cylinder having a central axis which is substantially parallel to said longitudinal axis of said lumen;

a sheath slideably disposed over said elongate member, said sheath slideable from a proximal position whereby an open distal end of said sheath is proximally displaced from said holes to a distal position whereby said distal end of said sheath is distally displaced from said plurality of holes, said sheath constructed and arranged to occlude said holes when positioned thereover.

2. The medical device of claim 1 wherein said elongate member comprises a hypodermic needle, said distal end sharpened to provide skin piercing or tissue entry capability.

3. The medical device of claim 1 wherein said elongate member comprises a catheter.

4. The medical device of claim 3 wherein said plurality of holes is axially displaced from said distal end.

5. The medical device of claim 1 wherein said distal end defines at least one hole of a predetermined diameter extending to said lumen.

6. The medical device of claim 1 wherein said distal end comprises a solid end wall.

7. The medical device of claim 1 wherein said sheath defines at least one opening positionable over one or more of said plurality of holes such that during an operation whereby injectate is being administered, predetermined holes may be selected, opened and reoccluded, thereby changing the shape of the cloud as desired.

8. The medical device of claim 1 wherein said sheath comprises a tapered distal end enabling said sheath to slide relative to and under surrounding tissue without imparting damage thereto.

9. The medical device of claim 1 wherein the elongate member comprises a scored outer surface such that injectate back pressure is minimized while injecting a liquid into tissue which is in contact with the outer surface of the member.

* * * * *